(12) United States Patent
Kaufmann

(10) Patent No.: US 6,589,745 B2
(45) Date of Patent: Jul. 8, 2003

(54) CIF130 INHIBITS CELL CYCLE PROGRESSION

(75) Inventor: Joerg Kaufmann, Berlin (DE)

(73) Assignee: Chiron Corporation, Emeryville, CA (US)

( * ) Notice: Subject to any disclaimer, the term of this patent is extended or adjusted under 35 U.S.C. 154(b) by 0 days.

(21) Appl. No.: 10/147,268

(22) Filed: May 15, 2002

(65) Prior Publication Data

US 2002/0143154 A1 Oct. 3, 2002

Related U.S. Application Data

(62) Division of application No. 09/709,979, filed on Nov. 9, 2000, now Pat. No. 6,423,822, which is a division of application No. 09/332,295, filed on Jun. 11, 1999, now Pat. No. 6,303,372.

(60) Provisional application No. 60/089,198, filed on Jun. 12, 1998, and provisional application No. 60/111,636, filed on Dec. 9, 1998.

(51) Int. Cl.$^7$ .............................. C12Q 1/68; C12Q 1/02; G01N 33/53

(52) U.S. Cl. ................................ 435/6; 435/7.1; 435/29

(58) Field of Search ................................ 435/6, 7.1, 29

(56) References Cited

U.S. PATENT DOCUMENTS 6,303,372 B1  10/2001  Kaufmann

FOREIGN PATENT DOCUMENTS

WO  WO 99/33985  7/1999
WO  WO 99/64450  12/1999

OTHER PUBLICATIONS

Kaufmann and Smale, "Direct recognition of initiator elements by a component of the transcription factor IID complex," *Genes & Development* 8(7):821–829, Apr. 1, 1994.

Kaufmann et al., "CIF150, a Human Cofactor for Transcription Factor IID–Dependent Initiator Function," *Molecular And Cellular Biology* 18(1):233–239, Jan. 1998.

Kaufmann et al., "CIF, an essential cofactor for TFIID–dependent initiator function," *Genes & Development* 10(7):873–886, Apr. 1, 1996.

Martin et al., "Human Transcription Factor hTAF$_{II}$150 (CIF150) Is Involved in Transcriptional Regulation of Cell Cycle Progression," *Molecular and Cellular Biology* 19(8):5548–5556, Aug. 1999.

Sukegawa et al., "A Putative Mammalian RNA Helicase with Arginine–Serine–Rich Domain Colocalizes with a Splicing Factor," *J. Biol. Chem.* 270(26):15702–15706, Jun. 30, 1995.

Sukegawa et al., EMBL Sequence Database, Accession No. ACQ62780, Nov. 1, 1996.

Suk et al., EMBL Sequence Database, Accession No. AC075619, Nov. 1, 1998.

*Primary Examiner*—Terry McKelvey
(74) *Attorney, Agent, or Firm*—Jane E. R. Potter; Kimberlin L. Morley; Robert P. Blackburn

(57) ABSTRACT

A human gene termed CIF130 and its expression products can alter the spatial or temporal patterns of mitosis or cell cycle progression of a human cell. Methods of treating disorders involving alterations in the regulation of mitosis or cell cycle progression utilize the gene and its expression product. Genes whose expression is dependent upon CIF130 expression can be identified.

16 Claims, 8 Drawing Sheets

```
        10        20        30        40        50        60        70        80        90
CGAAGGGGGCGGAGAGGAAGGAGCGCGGCGGGACCGGGCCGGGACAGCGCGTACTTTGGGCTCCGGGATTCGCTCCGCGCCCGCGGTTGT
GCTTCCCCGCCTCTCCTTCCTCGCGCCGCCCTGGCCCGGCCCTGTCGCGCATGAAACCCGAGGCCCTAAGCGAGGCGCGGGCGCCAACA
  R  R  G  R  R  G  R  S  A  A  G  P  G  R  D  S  A  Y  F  G  L  R  D  S  L  R  A  R  G  C>
                 TRANSLATION OF CIF 130 FULL LENGTH+30BP [A]                  >

100       110       120       130       140       150       160       170       180
AGCAGCTGCCGCTGCAGCCATAGCAGCAGGTCAGTCATTGGCACCATGAACTGGAATAAAGGTGGTCCTGGCACTAAGCGAGGATTTGGC
TCGTCGACGGCGACGTCGGTATCGTCGTCCAGTCAGTAACCGTGGTACTTGACCTTATTTCCACCAGGACCGTGATTCGCTCCTAAACCG
  S  S  C  R  C  S  H  S  S  R  S  V  I  G  T  M  N  W  N  K  G  G  P  G  T  K  R  G  F  G>
                 TRANSLATION OF CIF 130 FULL LENGTH+30BP [A]                  >

190       200       210       220       230       240       250       260       270
TTTGGAGGTTTTGCCATCAGTGCTGGGAAAAAGGAGGAACCCAAACTCCCACAGCAGTCCCACAGTGCCTTTGGGGCAACCAGCTCTTCT
AAACCTCCAAAACGGTAGTCACGACCCTTTTTCCTCCTTGGGTTTGAGGGTGTCGTCAGGGTGTCACGGAAACCCCGTTGGTCGAGAAGA
  F  G  G  F  A  I  S  A  G  K  K  E  E  P  K  L  P  Q  Q  S  H  S  A  F  G  A  T  S  S  S>
                 TRANSLATION OF CIF 130 FULL LENGTH+30BP [A]                  >

280       290       300       310       320       330       340       350       360
TCTGGATTTGGAAAGTCAGCTCCGCCACAGCTTCCTTCTTTCTACAAAATTGGATCTAAGCGGGCCAACTTTGATGAAGAAAATGCCTAT
AGACCTAAACCTTTCAGTCGAGGCGGTGTCGAAGGAAGAAAGATGTTTTAACCTAGATTCGCCCGGTTGAAACTACTTCTTTTACGGATA
  S  G  F  G  K  S  A  P  P  Q  L  P  S  F  Y  K  I  G  S  K  R  A  N  F  D  E  E  N  A  Y>
                 TRANSLATION OF CIF 130 FULL LENGTH+30BP [A]                  >

370       380       390       400       410       420       430       440       450
TTTGAAGATGAGGAAGAAGATTCTAGCAACGTTGATTTACCTTACATTCCTGCTGAAAACTCACCAACTCGCCAACAATTCCATTCCAAG
AAACTTCTACTCCTTCTTCTAAGATCGTTGCAACTAAATGGAATGTAAGGACGACTTTTGAGTGGTTGAGCGGTTGTTAAGGTAAGGTTC
  F  E  D  E  E  E  D  S  S  N  V  D  L  P  Y  I  P  A  E  N  S  P  T  R  Q  Q  F  H  S  K>
                 TRANSLATION OF CIF 130 FULL LENGTH+30BP [A]                  >

460       470       480       490       500       510       520       530       540
CCAGTAGATTCTGACAGCGATGATGATCCCTTGGAGGCATTCATGGCTGAGGTGGAGGATCAGGCGGCTAGAGACATGAAGAGGCTTGAA
GGTCATCTAAGACTGTCGCTACTACTAGGGAACCTCCGTAAGTACCGACTCCACCTCCTAGTCCGCCGATCTCTGTACTTCTCCGAACTT
  P  V  D  S  D  S  D  D  D  P  L  E  A  F  M  A  E  V  E  D  Q  A  A  R  D  M  K  R  L  E>
                 TRANSLATION OF CIF 130 FULL LENGTH+30BP [A]                  >

550       560       570       580       590       600       610       620       630
GAAAAGGACAAGGAAAGAAAAAACGTAAAGGGTATTCGAGATGACATTGAAGAGGAAGATGACCAAGAAGCTTATTTTCGATACATGGCA
CTTTTCCTGTTCCTTTCTTTTTTGCATTTCCCATAAGCTCTACTGTAACTTCTCCTTCTACTGGTTCTTCGAATAAAAGCTATGTACCGT
  E  K  D  K  E  R  K  N  V  K  G  I  R  D  D  I  E  E  E  D  D  Q  E  A  Y  F  R  Y  M  A>
                 TRANSLATION OF CIF 130 FULL LENGTH+30BP [A]                  >
```

*Fig. 1A*

```
         640       650       660       670       680       690       700       710       720
GAAAAACCCAACTGCTGGTGTGGTTCAGGAGGAAGAGGAAGACAATCTAGAATATGATAGTGACGGAAATCCAATTGCACCTACCAAAAAA
CTTTTGGGTTGACGACCACACCAAGTCCTCCTTCTCCTTCTGTTAGATCTTATACTATCACTGCCTTTAGGTTAACGTGGATGGTTTTTT
     E  N  P  T  A  G  V  V  Q  E  E  E  E  D  N  L  E  Y  D  S  D  G  N  P  I  A  P  T  K  K>
                    TRANSLATION OF CIF 130 FULL LENGTH+30BP [A]                         >

730       740       750       760       770       780       790       800       810
ATCATTGATCCTCTTCCCCCCATTGATCATTCAGAGATTGACTATCCACCATTTGAAAAAAACTTTTACAATGAGCATGAAGAGATAACC
TAGTAACTAGGAGAAGGGGGGTAACTAGTAAGTCTCTAACTGATAGGTGGTAAACTTTTTTTGAAAATGTTACTCGTACTTCTCTATTGG
     I  I  D  P  L  P  P  I  D  H  S  E  I  D  Y  P  P  F  E  K  N  F  Y  N  E  H  E  E  I  T>
                    TRANSLATION OF CIF 130 FULL LENGTH+30BP [A]                         >

820       830       840       850       860       870       880       890       900
AACCTCACTCCACAGCAGTTAATAGATCTCCGGCATAAGCTCAATCTTCGGGTCTCTGGTGCTGCACCTCCTAGACCAGGAAGTAGCTTT
TTGGAGTGAGGTGTCGTCAATTATCTAGAGGCCGTATTCGAGTTAGAAGCCCAGAGACCACGACGTGGAGGATCTGGTCCTTCATCGAAA
     N  L  T  P  Q  Q  L  I  D  L  R  H  K  L  N  L  R  V  S  G  A  A  P  P  R  P  G  S  S  F>
                    TRANSLATION OF CIF 130 FULL LENGTH+30BP [A]                         >

910       920       930       940       950       960       970       980       990
GCTCATTTTGGGTTTGACGAACAACTTATGCACCAGATTCGGAAATCTGAATACACACAGCCCACTCCAATACAGTGCCAGGGTGTGCCT
CGAGTAAAACCCAAACTGCTTGTTGAATACGTGGTCTAAGCCTTTAGACTTATGTGTGTCGGGTGAGGTTATGTCACGGTCCCACACGGA
     A  H  F  G  F  D  E  Q  L  M  H  Q  I  R  K  S  E  Y  T  Q  P  T  P  I  Q  C  Q  G  V  P>
                    TRANSLATION OF CIF 130 FULL LENGTH+30BP [A]                         >

1000      1010      1020      1030      1040      1050      1060      1070      1080
GTGGCATTAAGTGGTAGAGACATGATTGGTATTGCCAAAACAGGTAGTGGGAAAACTGCAGCCTTCATTTGGCCCATGTTGATTCATATA
CACCGTAATTCACCATCTCTGTACTAACCATAACGGTTTTGTCCATCACCCTTTTGACGTCGGAAGTAAACCGGGTACAACTAAGTATAT
     V  A  L  S  G  R  D  M  I  G  I  A  K  T  G  S  G  K  T  A  A  F  I  W  P  M  L  I  H  I>
                    TRANSLATION OF CIF 130 FULL LENGTH+30BP [A]                         >

1090      1100      1110      1120      1130      1140      1150      1160      1170
ATGGACCAGAAGGAGTTGGAACCAGGTGATGGACCAATTGCAGTGATTGTGTGTCCTACCAGGGAGCTTTGCCAGCAGATCCATCCAGAA
TACCTGGTCTTCCTCAACCTTGGTCCACTACCTGGTTAACGTCACTAACACACAGGATGGTCCCTCGAAACGGTCGTCTAGGTAGGTCTT
     M  D  Q  K  E  L  E  P  G  D  G  P  I  A  V  I  V  C  P  T  R  E  L  C  Q  Q  I  H  P  E>
                    TRANSLATION OF CIF 130 FULL LENGTH+30BP [A]                         >

1180      1190      1200      1210      1220      1230      1240      1250      1260
TGTAAGCGGTTTGGAAAAGCATATAATCTTCGATCAGTGGCCGTATATGGAGGAGGGAGTATGTGGGAGCAGGCCAAGGCCCTTCAGGAG
ACATTCGCCAAACCTTTTCGTATATTAGAAGCTAGTCACCGGCATATACCTCCTCCCTCATACACCCTCGTCCGGTTCCGGGAAGTCCTC
     C  K  R  F  G  K  A  Y  N  L  R  S  V  A  V  Y  G  G  G  S  M  W  E  Q  A  K  A  L  Q  E>
                    TRANSLATION OF CIF 130 FULL LENGTH+30BP [A]                         >
```

*Fig. 1B*

```
      1270      1280      1290      1300      1310      1320      1330      1340      1350
GGGGCAGAGATTGTTGTGTGTACCCCAGGTCGACTGATAGATCATGTGAAAAAGAAAGCTACCAATCTTCAAAGAGTCTCTTACCTTGTG
CCCCGTCTCTAACAACACACATGGGGTCCAGCTGACTATCTAGTACACTTTTTCTTTCGATGGTTAGAAGTTTCTCAGAGAATGGAACAC
  G  A  E  I  V  V  C  T  P  G  R  L  I  D  H  V  K  K  K  A  T  N  L  Q  R  V  S  Y  L  V>
_____TRANSLATION OF CIF 130 FULL LENGTH+30BP [A]_____>

1360      1370      1380      1390      1400      1410      1420      1430      1440
TTTGATGAAGCAGATCGAATGTTTGACATGGGATTTGAGTACCAAGTTCGATCCATAGCAAGTCATGTTCGTCCTGACAGGCAGACTCTC
AAACTACTTCGTCTAGCTTACAAACTGTACCCTAAACTCATGGTTCAAGCTAGGTATCGTTCAGTACAAGCAGGACTGTCCGTCTGAGAG
  F  D  E  A  D  R  M  F  D  M  G  F  E  Y  Q  V  R  S  I  A  S  H  V  R  P  D  R  Q  T  L>
_____TRANSLATION OF CIF 130 FULL LENGTH+30BP [A]_____>

1450      1460      1470      1480      1490      1500      1510      1520      1530
TTATTTAGTGCAACTTTTCGGAAGAAGATTGAAAAGTTGGCCAGAGACATCCTGATCGACCCTATTCGAGTGGTGCAGGGAGATATTGGA
AATAAATCACGTTGAAAAGCCTTCTTCTAACTTTTCAACCGGTCTCTGTAGGACTAGCTGGGATAAGCTCACCACGTCCCTCTATAACCT
  L  F  S  A  T  F  R  K  K  I  E  K  L  A  R  D  I  L  I  D  P  I  R  V  V  Q  G  D  I  G>
_____TRANSLATION OF CIF 130 FULL LENGTH+30BP [A]_____>

1540      1550      1560      1570      1580      1590      1600      1610      1620
GAGGCAAATGAAGATGTGACACAGATTGTGGAGATTCTCCATTCTGGACCTAGTAAATGGAACTGGCTTACCCGGCGTCTGGTAGAATTT
CTCCGTTTACTTCTACACTGTGTCTAACACCTCTAAGAGGTAAGACCTGGATCATTTACCTTGACCGAATGGGCCGCAGACCATCTTAAA
  E  A  N  E  D  V  T  Q  I  V  E  I  L  H  S  G  P  S  K  W  N  W  L  T  R  R  L  V  E  F>
_____TRANSLATION OF CIF 130 FULL LENGTH+30BP [A]_____>

1630      1640      1650      1660      1670      1680      1690      1700      1710
ACCTCTTCAGGGAGTGTCCTCCTCTTTGTTACTAAAAAAGCCAATGCTGAAGAGCTAGCGAATAACCTTAAACAGGAGGGTCATAATCTT
TGGAGAAGTCCCTCACAGGAGGAGAAACAATGATTTTTTCGGTTACGACTTCTCGATCGCTTATTGGAATTTGTCCTCCCAGTATTAGAA
  T  S  S  G  S  V  L  L  F  V  T  K  K  A  N  A  E  E  L  A  N  N  L  K  Q  E  G  H  N  L>
_____TRANSLATION OF CIF 130 FULL LENGTH+30BP [A]_____>

1720      1730      1740      1750      1760      1770      1780      1790      1800
GGGCTGCTCCATGGGGATATGGATCAGAGTGAGAGAAACAAGGTCATTTCAGACTTTAAGAAAAAGGACATCCCAGTCCTGGTGGCCACA
CCCGACGAGGTACCCCTATACCTAGTCTCACTCTCTTTGTTCCAGTAAAGTCTGAAATTCTTTTTCCTGTAGGGTCAGGACCACCGGTGT
  G  L  L  H  G  D  M  D  Q  S  E  R  N  K  V  I  S  D  F  K  K  K  D  I  P  V  L  V  A  T>
_____TRANSLATION OF CIF 130 FULL LENGTH+30BP [A]_____>

1810      1820      1830      1840      1850      1860      1870      1880      1890
GATGTTGCAGCCCGTGGTCTGGACATTCCTTCAATTAAGACTGTCATTAACTATGATGTGGCACGGGACATTGATACGCACACTCACAGG
CTACAACGTCGGGCACCAGACCTGTAAGGAAGTTAATTCTGACAGTAATTGATACTACACCGTGCCCTGTAACTATGCGTGTGAGTGTCC
  D  V  A  A  R  G  L  D  I  P  S  I  K  T  V  I  N  Y  D  V  A  R  D  I  D  T  H  T  H  R>
_____TRANSLATION OF CIF 130 FULL LENGTH+30BP [A]_____>
```

*Fig. 1C*

```
         1900      1910      1920      1930      1940      1950      1960      1970      1980
ATTGGCCGCACAGGAAGAGCGGGTGAGAAAGGTGTGGCCTATACCCTACTCACTCCCAAGGACAGCAATTTTGCTGGTGACCTGGTCCGG
TAACCGGCGTGTCCTTCTCGCCCACTCTTTCCACACCGGATATGGGATGAGTGAGGGTTCCTGTCGTTAAAACGACCACTGGACCAGGCC
   I  G  R  T  G  R  A  G  E  K  G  V  A  Y  T  L  L  T  P  K  D  S  N  F  A  G  D  L  V  R>
                _____TRANSLATION OF CIF 130 FULL LENGTH+30BP [A]_____>

1990      2000      2010      2020      2030      2040      2050      2060      2070
AACTTGGAAGGAGCCAATCAACACGTTTCTAAGGAACTCCTAGATCTGGCAATGCAGAATGCCTGGTTTCGGAAATCTCGATTCAAAGGA
TTGAACCTTCCTCGGTTAGTTGTGCAAAGATTCCTTGAGGATCTAGACCGTTACGTCTTACGGACCAAAGCCTTTAGAGCTAAGTTTCCT
   N  L  E  G  A  N  Q  H  V  S  K  E  L  L  D  L  A  M  Q  N  A  W  F  R  K  S  R  F  K  G>
                _____TRANSLATION OF CIF 130 FULL LENGTH+30BP [A]_____>

2080      2090      2100      2110      2120      2130      2140      2150      2160
GGGAAAGGAAAAAAGCTGAACATTGGTGGAGGAGGCCTAGGCTACAGGGAGCGGCCTGGCCTGGGCTCTGAGAACATGGATCGAGGAAAT
CCCTTTCCTTTTTTCGACTTGTAACCACCTCCTCCGGATCCGATGTCCCTCGCCGGACCGGACCCGAGACTCTTGTACCTAGCTCCTTTA
   G  K  G  K  K  L  N  I  G  G  G  G  L  G  Y  R  E  R  P  G  L  G  S  E  N  M  D  R  G  N>
                _____TRANSLATION OF CIF 130 FULL LENGTH+30BP [A]_____>

2170      2180      2190      2200      2210      2220      2230      2240      2250
AACAATGTAATGAGCAATTATGAGGCCTACAAGCCTTCCACAGGAGCTATGGGAGATCGACTAACGGCAATGAAAGCAGCTTTCCAGTCA
TTGTTACATTACTCGTTAATACTCCGGATGTTCGGAAGGTGTCCTCGATACCCTCTAGCTGATTGCCGTTACTTTCGTCGAAAGGTCAGT
   N  N  V  M  S  N  Y  E  A  Y  K  P  S  T  G  A  M  G  D  R  L  T  A  M  K  A  A  F  Q  S>
                _____TRANSLATION OF CIF 130 FULL LENGTH+30BP [A]_____>

2260      2270      2280      2290      2300      2310      2320      2330      2340
CAGTACAAGAGTCACTTTGTTGCAGCCAGTTTAAGTAATCAGAAGGCTGGAAGTTCTGCTGCCGGGGCAAGTGGGTGGACTAGTGCAGGG
GTCATGTTCTCAGTGAAACAACGTCGGTCAAATTCATTAGTCTTCCGACCTTCAAGACGACGGCCCCGTTCACCCACCTGATCACGTCCC
   Q  Y  K  S  H  F  V  A  A  S  L  S  N  Q  K  A  G  S  S  A  A  G  A  S  G  W  T  S  A  G>
                _____TRANSLATION OF CIF 130 FULL LENGTH+30BP [A]_____>

2350      2360      2370      2380      2390      2400      2410      2420      2430
AGCTTGAATTCTGTTCCAACTAACTCAGCACAACAGGGCCATAACAGTCCTGACAGCCCCGTCACCAGTGCCGCCAAGGGCATCCCAGGC
TCGAACTTAAGACAAGGTTGATTGAGTCGTGTTGTCCCGGTATTGTCAGGACTGTCGGGGCAGTGGTCACGGCGGTTCCCGTAGGGTCCG
   S  L  N  S  V  P  T  N  S  A  Q  Q  G  H  N  S  P  D  S  P  V  T  S  A  A  K  G  I  P  G>
                _____TRANSLATION OF CIF 130 FULL LENGTH+30BP [A]_____>

2440      2450      2460      2470      2480      2490      2500      2510      2520
TTTGGCAATACTGGCAACATCAGTGGTGCCCCTGTGACCTACCCGTCTGCCGGAGCCCAAGGAGTCAACAACACAGCTTCAGGGAATAAC
AAACCGTTATGACCGTTGTAGTCACCACGGGGACACTGGATGGGCAGACGGCCTCGGGTTCCTCAGTTGTTGTGTCGAAGTCCCTTATTG
   F  G  N  T  G  N  I  S  G  A  P  V  T  Y  P  S  A  G  A  Q  G  V  N  N  T  A  S  G  N  N>
                _____TRANSLATION OF CIF 130 FULL LENGTH+30BP [A]_____>
```

*Fig. 1D*

```
       2530      2540      2550      2560      2570      2580      2590      2600      2610
AGCCGAGAAGGGACTGGGGGCAGCAACGGGAAAAGGGAGAGATATACTGAGAACCGGGGCAGCAGCCGTCACAGTCACGGAGAGACTGGC
TCGGCTCTTCCCTGACCCCCGTCGTTGCCCTTTTCCCTCTCTATATGACTCTTGGCCCCGTCGTCGGCAGTGTCAGTGCCTCTCTGACCG
    S  R  E  G  T  G  G  S  N  G  K  R  E  R  Y  T  E  N  R  G  S  S  R  H  S  H  G  E  T  G>
                    TRANSLATION OF CIF 130 FULL LENGTH+30BP [A]                       >

2620      2630      2640      2650      2660      2670      2680      2690      2700
AATCGGCATAGCGATAGTCCACGTCACGGAGATGGTGGTCGCCATGGAGATGGATACCGCCATCCAGAAAGCAGCAGCCGTCATACTGAT
TTAGCCGTATCGCTATCAGGTGCAGTGCCTCTACCACCAGCGGTACCTCTACCTATGGCGGTAGGTCTTTCGTCGTCGGCAGTATGACTA
    N  R  H  S  D  S  P  R  H  G  D  G  G  R  H  G  D  Y  R  H  P  E  S  S  S  R  H  T  D>
                    TRANSLATION OF CIF 130 FULL LENGTH+30BP [A]                       >

2710      2720      2730      2740      2750      2760      2770      2780      2790
GGCCATCGGCACGGGGAGAACAGACATGGAGGAAGCGCAGGCCGGCATGGGGAGAACCGGGGTGCAAATGATGGTCGGAATGGGGAAAGC
CCGGTAGCCGTGCCCCTCTTGTCTGTACCTCCTTCGCGTCCGGCCGTACCCCTCTTGGCCCCACGTTTACTACCAGCCTTACCCCTTTCG
    G  H  R  H  G  E  N  R  H  G  G  S  A  G  R  H  G  E  N  R  G  A  N  D  G  R  N  G  E  S>
                    TRANSLATION OF CIF 130 FULL LENGTH+30BP [A]                       >

2800      2810      2820      2830      2840      2850      2860      2870      2880
AGGAAAGAAGCTTTTAATCGTGAGGGCAAGATGGAGCCCAAGATGGAACCCAAAGCGGACAGCAGCAAGATGGACAAGGTGGACAGCAAG
TCCTTTCTTCGAAAATTAGCACTCCCGTTCTACCTCGGGTTCTACCTTGGGTTTCGCCTGTCGTCGTTCTACCTGTTCCACCTGTCGTTC
    R  K  E  A  F  N  R  E  G  K  M  E  P  K  M  E  P  K  A  D  S  S  K  M  D  K  V  D  S  K>
                    TRANSLATION OF CIF 130 FULL LENGTH+30BP [A]                       >

2890      2900      2910      2920      2930      2940      2950      2960      2970
ACAGATAAGACAGCTGACGGTTTTGCTGTCCCAGAGCCGCCTAAACGCAAGAAAGGTCGATGGGACAGTTAGAGGGGATGTGCTAAAGCG
TGTCTATTCTGTCGACTGCCAAAACGACAGGGTCTCGGCGGATTTGCGTTCTTTCCAGCTACCCTGTCAATCTCCCCTACACGATTTCGC
    T  D  K  T  A  D  G  F  A  V  P  E  P  P  K  R  K  K  G  R  W  D  S  *  R  G  C  A  K  A>
                    TRANSLATION OF CIF 130 FULL LENGTH+30BP [A]                       >

2980      2990      3000      3010      3020      3030      3040      3050      3060
TGAAATCAGTTGTCCTTAATTTTTAGAAAGATTTTGGTAACTAGGTGTCTCAGGGCTGGGTTGGGGTCCAAAGTGTAAGGACCCCCTGCC
ACTTTAGTCAACAGGAATTAAAAATCTTTCTAAAACCATTGATCCACAGAGTCCCGACCCAACCCCAGGTTTCACATTCCTGGGGGACGG
    *  N  Q  L  S  L  I  F  R  K  I  L  V  T  R  C  L  R  A  G  L  G  S  K  V  *  G  P  P  A>
                    TRANSLATION OF CIF 130 FULL LENGTH+30BP [A]                       >

3070      3080      3090      3100      3110      3120      3130      3140      3150
CTTAGTGGAGAGCTGGAGCTTGGAGACATTACCCCTTCATCAGAAGGAATTTTCGGATGTTTTCTTGGGAAGCTGTTTTGGTCCTTGGAA
GAATCACCTCTCGACCTCGAACCTCTGTAATGGGGAAGTAGTCTTCCTTAAAAGCCTACAAAAGAACCCTTCGACAAAACCAGGAACCTT
    L  S  G  E  L  E  L  G  D  I  T  P  S  S  E  G  I  F  G  C  F  L  G  K  L  F  W  S  L  E>
                    TRANSLATION OF CIF 130 FULL LENGTH+30BP [A]                       >
```

*Fig. 1E*

```
         3160      3170      3180      3190      3200      3210      3220      3230      3240
GCAGTGAGAGCTGGGAAGCTTCTTTTGGCTCTAGGTGAGTTGTCATGCGGGTAAGTTGAGGTTATCTTGGGATAAAGGGTCTTCTAGGGC
CGTCACTCTCGACCCTTCGAAGAAAACCGAGATCCACTCAACAGTACGCCCATTCAACTCCAATAGAACCCTATTTCCCAGAAGATCCCG
    A  V  R  A  G  K  L  L  L  A  L  G  E  L  S  C  G  *  V  E  V  I  L  G  *  R  V  F  *  G>
                    ___TRANSLATION OF CIF 130 FULL LENGTH+30BP [A]_____>

3250      3260      3270      3280      3290      3300      3310      3320      3330
ACAAAACTCACTCTAGGTTTATATTATATGTAGCTTATATTTTTTACTAAGGTGTCACCTTATAAGCATCTATAAATTGAGTTCTTTTTC
TGTTTTGAGTGAGATCCAAATATAATATACATCGAATATAAAAAATGATTCCACAGTGGAATATTCGTAGATATTTAACTCAAGAAAAAG
    T  K  L  T  L  G  L  Y  Y  M  *  L  I  F  F  T  K  V  S  P  Y  K  H  L  *  I  E  F  F  F>
                    ___TRANSLATION OF CIF 130 FULL LENGTH+30BP [A]_____>

3340      3350      3360      3370      3380      3390      3400      3410      3420
TTAGTTGTATGGCCAGGCAGTCCCCATTTTAGGAGTTGGCTTCTGCAAATTCAATCCATTGAGCTAACTGTTGGGGAGCAATTTGGTAGT
AATCAACATACCGGTCCGTCAGGGGTAAAATCCTCAACCGAAGACGTTTAAGTTAGGTAACTCGATTGACAACCCCTCGTTAAACCATCA
    L  V  V  W  P  G  S  P  H  F  R  S  W  L  L  Q  I  Q  S  I  E  L  T  V  G  E  Q  F  G  S>
                    ___TRANSLATION OF CIF 130 FULL LENGTH+30BP [A]_____>

3430      3440      3450      3460      3470      3480      3490      3500      3510
TGTAGACATTTGCAGGGAAGGGAGATGTCTGATTCTAAATGGGAGTTGATGCTCAGGTCCCCAGCCAGGTTTGCATCCAGCCCTGAGACA
ACATCTGTAAACGTCCCTTCCCTCTACAGACTAAGATTTACCCTCAACTACGAGTCCAGGGGTCGGTCCAAACGTAGGTCGGGACTCTGT
    C  R  H  L  Q  G  R  E  M  S  D  S  K  W  E  L  M  L  R  S  P  A  R  F  A  S  S  P  E  T>
                    ___TRANSLATION OF CIF 130 FULL LENGTH+30BP [A]_____>

3520      3530      3540      3550      3560      3570      3580      3590      3600
TGTAGGAAACACCTTTCAGACCCAGGCTCTGAAGATTCCCAGAAGCCACAAGGATTGAAGGGAAAAGGTGATCCTGGTAACTGTTCCAGG
ACATCCTTTGTGGAAAGTCTGGGTCCGAGACTTCTAAGGGTCTTCGGTGTTCCTAACTTCCCTTTTCCACTAGGACCATTGACAAGGTCC
    C  R  K  H  L  S  D  P  G  S  E  D  S  Q  K  P  Q  G  L  K  G  K  G  D  P  G  N  C  S  R>
                    ___TRANSLATION OF CIF 130 FULL LENGTH+30BP [A]_____>

3610      3620      3630      3640      3650      3660      3670      3680      3690
ATTGCTCCAGGTTTGAGATGGTATTGCTAAAATTTAAAATTAAACAAGAGACCCAACAACAGCTTTTAAAGTGTCTTCTATTTCATTGTAT
TAACGAGGTCCAAACTCTACCATAACGATTTAAATTTTAATTTGTTCTCTGGGTTGTTGTCGAAAATTTCACAGAAGATAAAGTAACATA
    I  A  P  G  L  R  W  Y  C  *  I  *  N  *  T  R  D  P  T  T  A  F  K  V  S  S  I  S  L  Y>
                    ___TRANSLATION OF CIF 130 FULL LENGTH+30BP [A]_____>

3700      3710      3720      3730      3740      3750      3760      3770      3780
TTTTTTTAACTTGCCCCAATGATAGAAAAGTCTTTTGCTGAAATGATTTTGATGATTTTTGTTTATCGTTTATAAAAAGGAAAAGAAATA
AAAAAAATTGAACGGGGTTACTATCTTTTCAGAAAACGACTTTACTAAAACTACTAAAAACAAATAGCAAATATTTTTCCTTTTCTTTAT
    F  F  *  L  A  P  M  I  E  K  S  F  A  E  M  I  L  M  I  F  V  Y  R  L  *  K  G  K  E  I>
                    ___TRANSLATION OF CIF 130 FULL LENGTH+30BP [A]_____>

3790      3800      3810      3820
TAAAAAAAAAAAAAAAAAAAAAAAAAAAAAAAGCGGCCGCTGAATTC
ATTTTTTTTTTTTTTTTTTTTTTTTTTTTTTTCGCCGGCGACTTAAG
    *  K  K  K  K  K  K  K  K  K  A  A  A  E  F>
    __TRANSLATION OF CIF 130 FULL LENGTH+30B___>
```

*Fig. 1F*

```
   1 CAAGATGTCG GCGGATGGTA GCTTCGAGCC CTTGCGGAGA GGAGCATCTC TGTGACAGAA
  61 GCTTGTCGAC GGCGGCTTCT AGGAGCTAGT CGAAGGAGCG AGGTTGAGGC GGGCAGCGAC
 121 CCGTCAGGTC GCTCACCTGG GCACCGGCCA GCTGCGAGAC GTGACTTGGG GACCGCAGGG
 181 GAGTGGAGAG TGTGAGGTGC CAAAGACTAG TAATGCCCCG TATCCCCCTA GGAAGCCGGG
 241 AAGCCAAGCT CCGCGGGACC GCTTCATGCC GCTGACTGGT GTAGAGCCCG CCAGAATGAA
 301 CAGGAAGAAA GGAGACAAGG GCTTTGAAAG CCCAAGGCCA TATAAATTAA CCCATCAGGT
 361 CGTCTGCATC AACAACATAA ATTTCCACAG AAAATCTGTT GTGGGATTTG TGGAACTGAC
 421 TATATTCCCC ACAGTTGCAA ACTTGAATAG AATCAAGTTG AACAGCAAAC AGTGTAGAAT
 481 ATACCGAGTA AGGATCAATG ATTTAGAGGC TGCTTTTATT TATAATGACC CAACCTTGGA
 541 AGTTTGTCAC AGTGAATCAA AACAGAGAAA CCTCAATTAT TTTTCCAATG CTTATGCAGC
 601 TGCAGTTAGT GCTGTGGACC CTGATGCAGG AAATGGAGAA CTTTGCATTA AGGTTCCATC
 661 AGAGCTATGG AAACACGTTG ATGAGTTAAA GGTCCTGAAG ATACACATCA ATTTTTCTTT
 721 GGATCAGCCC AAAGGAGGTC TTCATTTTGT GGTACCCAGT GTAGAGGGAA GTATGGCAGA
 781 GAGAGGTGCT CATGTTTTCT CTTGTGGGTA TCAAAATTCT ACAAGATTTT GGTTCCCTTG
 841 TGTTGATTCA TACTCTGAAT TGTGTACATG GAAATTAGAA TTTACAGTAG ATGCTGCAAT
 901 GGTTGCTGTT TCTAATGGCG ATTTGGTGGA GACAGTGTAT ACTCATGATA TGAGGAAGAA
 961 AACTTTCCAT TATATGCTTA CCATTCCTAC AGCAGCGTCA AATATCTCCT TGGCCATTGG
1021 ACCATTTGAA ATACTGGTAG ATCCATACAT GCATGAGGTT ACTCATTTTT GTTTGCCCCA
1081 ACTTCTTCCA TTGCTGAAAC ATACCACATC ATACCTTCAT GAAGTCTTTG AATTTTATGA
1141 AGAAATTCTT ACATGTCGTT ACCCATACTC CTGTTTTAAG ACTGTCTTCA TTGATGAGGC
1201 TTATGTTGAA GTGGCTGCTT ATGCTTCCAT GAGCATTTTT AGCACAAATC TTTTACACAG
1261 TGCCATGATT ATAGATGAGA CACCTTTGAC TAGAAGGTGT TTAGCCCAAT CCTTGGCCCA
1321 GCAGTTTTTT GGTTGTTTCA TATCTAGAAT GTCTTGGTCT GATGAATGGG TGCTGAAGGG
1381 AATTTCAGGC TATATCTATG GACTTTGGAT GAAAAAAACT TTTGGTGTTA ATGAGTACCG
1441 CCATTGGATT AAAGAGGAGC TAGACAAAAT AGTGGCATAT GAACTAAAAA CTGGTGGGGT
1501 TTTACTACAT CCCATATTTG GTGGAGGAAA AGAGAAGGAT AATCCGGCTT CCCATCTACA
1561 CTTTTCAATA AAGCATCCAC ATACACTGTC CTGGGAATAC TACACTATGT TTCAGTGTAA
1621 AGCCCACCTT GTGATGAGAT TGATTGAAAA TAGGATCAGT ATGGAATTTA TGCTACAAGT
1681 TTTCAATAAA CTGCTAAGTC TGGCTAGTAC TGCTTCATCT CAGAAGTTCC AGTCACATAT
1741 GTGGAGTCAG ATGTTGGTTT CCACATCTGG GTTTTTGAAA TCCATTTCAA ATGTCTCTGG
1801 CAAAGATATT CAGCCGTTAA TAAAGCAGTG GGTAGATCAG AGTGGAGTGG TAAAATTTTA
1861 TGGAAGTTTT GCATTTAATA GAAAACGAAA TGTCTTGGAA CTGGAAATAA AACAGGACTA
1921 TACATCTCCT GGAACTCAGA AATACGTGGG ACCACTTAAA GTGACAGTGC AGGAGTTAGA
1981 TGGATCCTTC AATCATACAC TGCAAATTGA AGAAAACAGC CTTAAACATG ATATACCCTG
2041 CCATTCCAAA AGTAGAAGGA ATAAAAAGAA AAAAATCCCA CTGATGAATG GAGAAGAAGT
2101 TGATATGGAT CTTTCTGCAA TGGATGCTGA TTCCCCTTTG CTGTGGATAA GGATAGACCC
2161 AGATATGTCA GTATTGAGGA AGGTAGAATT TGAGCAAGCT GATTTTATGT GGCAGTATCA
2221 GCTCCGCTAT GAGAGAGATG TTGTTGCACA GCAGGAATCC ATTTTGGCTT TGGAAAAATT
2281 CCCTACTCCA GCATCTCGGC TTGCACTCAC TGATATATTA GAACAAGAGC AGTGTTTCTA
2341 CAGAGTAAGA ATGTCAGCTT GTTTCTGTCT TGCAAAGATT GCAAATTCAA TGGTGAGCAC
2401 ATGGACAGGA CCACCAGCCA TGAAGTCACT CTTCACTAGG ATGTTTTGTT GTAAAAGTTG
2461 TCCAAACATT GTGAAAACAA ACAACTTTAT GAGCTTTCAA AGCTATTTTC TACAGAAGAC
2521 TATGCCAGTT GCAATGGCTT TATTAAGAGA TGTTCATAAT CTTTGTCCTA AAGAAGTCTT
```

*Fig. 2A*

```
2581 AACATTTATT TTAGACTTAA TCAAGTACAA TGACAACAGG AAAAATAAGT TTTCAGATAA
2641 CTATTATCGT GCAGAAATGA TTGATGCCCT GGCCAACTCT GTTACACCTG CAGTCAGTGT
2701 GAATAATGAA GTTAGAACTT TGGATAACTT AAATCCTGAT GTGCGACTCA TTCTTGAAGA
2761 AATCACCAGA TTTTTGAATA TGGAAAAACT TCTTCCGAGT TACAGGCATA CCATCACTGT
2821 CAGTTGTTTG AGAGCCATAC GGGTACTTCA GAAGAACGGA CATGTGCCAA GTGATCCAGC
2881 TCTTTTTAAA TCTTATGCTG AATATGGCCA CTTTGTGGAC ATTAGGATAG CAGCTTTGGA
2941 AGCAGTTGTT GATTATACTA AAGTGGACAG AAGTTATGAA GAACTGCAAT GGCTACTTAA
3001 TATGATTCAG AATGACCCTG TACCCTATGT AAGGCATAAG ATTCTCAACA TGTTGACTAA
3061 GAACCCCCCA TTTACTAAGA ACATGGAGTC TCCCTTATGC AATGAAGCCC TGGTAGATCA
3121 ACTTTGGAAA CTTATGAATT CTGGTACTTC ACATGACTGG AGGTTACGGT GTGGTGCTGT
3181 GGACTTGTAC TTCACACTTT TTGGCCTCAG TAGACCTTCC TGTTTACCCT TGCCAGAGCT
3241 TGGGTTGGTT CTTAATCTAA AGGAGAAAAA AGCTGTCTTG AATCCTACCA TAATTCCAGA
3301 GTCAGTAGCA GGCAACCAAG AAGCTGCAAA TAATCCAAGC AGTCACCCAC AGCTAGTTGG
3361 ATTTCAGAAC CCTTTTTCCA GTTCTCAAGA TGAGGAGGAG ATTGATATGG ATACTGTTCA
3421 TGATAGCCAG GCCTTCATTT CCCATCATTT AAACATGCTT GAAAGGCCGT CAACTCCAGG
3481 GCTCTCGAAA TATCGGCCAG CTAGCTCCCG ATCTGCTTTA ATACCCCAGC ACTCAGCAGG
3541 CTGTGACAGC ACACCCACCA CAAAACCCCA GTGGAGTTTG GAACTTGCAC GGAAGGGAAC
3601 AGGTAAAGAA CAAGCACCTT TGGAGATGAG TATGCATCCA GCGGCAAGCG CTCCACTCTC
3661 AGTCTTTACT AAGGAATCTA CAGCCTCCAA ACACAGTGAC CACCATCACC ACCATCACCA
3721 TGAGCACAAG AAAAAGAAGA AGAAGCATAA ACATAAGCAC AAACACAAGC ATAAGCATGA
3781 CAGTAAAGAA AAGGACAAGG AGCCTTTCAC TTTCTCCAGC CCTGCCAGTG GCAGGTCTAT
3841 TCGTTCTCCT TCCCTTTCAG ACTGAGAAGG GGACAAAAAG ACCTTTCCTT TCATGTCCAG
3901 AAGAATGTAT GTAACTAAAG CTTTGTCCTC TGTGAAGAAT TATAAATGGA GGGGGGAAAG
3961 GATTCGCCTC TCCTACAGAA ATTCTGAATT CATTTAA
```

*Fig. 2B*

```
MPLTGVEPARMNRKKGDKGFESPRPYKLTHQVVCINNINFHRKSVVGFVELTIFPTVANLNRIKLNSKQCRIYRVRINDLEAAFIYND
PTLEVCHSESKQRNLNYFSNAYAAAVSAVDPDAGNGELCIKVPSELWKHVDELKVLKIHINFSLDQPKGGLHFVVPSVEGSMAERGAH
VFSCGYQNSTRFWFPCVDSYSELCTWKLEFTVDAAMVAVSNGDLVETVYTHDMRKKTFHYMLTIPTAASNISLAIGPFEILVDPYMHE
VTHFCLPQLLPLLKHTTSYLHEVFEFYEEILTCRYPYSCFKTVFIDEAYVEVAAYASMSIFSTNLLHSAMIIDETPLTRRCLAQSLAQ
QFFGCFISRMSWSDEWVLKGISGYIYGLWMKKTFGVNEYRHWIKEELDKIVAYELKTGGVLLHPIFGGGKEKDNPASHLHFSIKHPHT
LSWEYYTMFQCKAHLVMRLIENRISMEFMLQVFNKLLSLASTASSQKFQSHMWSQMLVSTSGFLKSISNVSGKDIQPLIKQWVDQSGV
VKFYGSFAFNKRKRNVLELEIKQDYTSPGTQKYVGPLKVTVQELDGSFNHTLQIEENSLKHDIPCHSKSRRNKKKKIPLMNGEEVDMDL
SAMDADSPLLWIRIDPDMSVLRKVEFEQADFMWQYQLRYERDVVAQQESILALEKFPTPASRLALTDILEQEQCFYRVRMSACFCLAK
IANSMVSTWTGPPAMKSLFTRMFCCKSCPNIVKTNNFMSFQSYFLQKTMPVAMALLRDVHNLCPKEVLTFILDLIKYNDNRKNKFSDN
YYRAEMIDALANSVTPAVSVNNEVRTLDNLNPDVRLILEEITRFLNMEKLLPSYRHTITVSCLRAIRVLQKNGHVPSDPALFKSYAEY
GHFVDIRIAALEAVVDYTKVDRSYEELQWLLNMIQNDPVPYVRHKILNMLTKNPPFTKNMESPLCNEALVDQLWKLMNSGTSHDWRLR
CGAVDLYFTLFGLSRPSCLPLPELGLVLNLKEKKAVLNPTIIPESVAGNQEAANNPSSHPQLVGFQNPFSSSQDEEEIDMDTVHDSQA
FISHHLNMLERPSTPGLSKYRPASSRSALIPQHSAGCDSTPTTKPQWSLELARKGTGKEQAPLEMSMHPAASAPLSVFTKESTASKHS
DHHHHHHEHKKKKKKHKHKHKHKHKHKHDSKEKDKEPFTFSSPASGRSIRSPSLSD
```

*Fig. 3*

CIF130 INHIBITS CELL CYCLE PROGRESSION

CROSS-REFERENCE TO RELATED APPLICATIONS

This application is a divisional of U.S. patent application Ser. No. 09/709,979, filed Nov. 9, 2000, now U.S. Pat. No. 6,423,822; which is a divisional of U.S. patent application Ser. No. 09/332,295 filed Jun. 11, 1999, now U.S. Pat. No. 6,303,372; which application claims the benefit of provisional applications Ser. No. 60/089,198 filed Jun. 12, 1998, and Ser. No. 60/111,636 filed Dec. 9, 1998, which are incorporated by reference herein in their entirety.

TECHNICAL AREA OF THE INVENTION

The invention relates to the area of cell cycle progression. More particularly, the invention relates to proteins which regulate cell cycle progression.

BACKGROUND OF THE INVENTION

Alterations in the regulation of cell cycle progression play an important role in diseases such as neoplasia and anemia. Manipulation of genes involved in regulating the cell cycle can be used to prevent or treat these diseases. Detections of mutations in cell-cycle regulatory genes can also be used to detect neoplastic cells and genetic predispositions to neoplasias. Thus, there is a need in the art for the identification of cell cycle regulator genes which can be used in methods of diagnosing, prognosing, and treating neoplasia and other diseases in humans and other mammals.

SUMMARY OF THE INVENTION

It is an object of the invention to provide reagents and methods for regulating mitosis or cell cycle progression in human cells and for treating disorders related to alterations in cell cycle progression. These and other objects of the invention are provided by one or more of the embodiments described below.

One embodiment of the invention is an isolated and purified human CIF130 protein comprising an amino acid sequence which is at least 85% identical to the amino acid sequence shown in SEQ ID NO:2. Percent identity is determined using a Smith-Waterman homology search algorithm using an affine gap search with a gap open penalty of 12 and a gap extension penalty of 1.

Another embodiment of the invention is an isolated polypeptide comprising at least 17 contiguous amino acids as shown in SEQ ID NO:2.

Yet another embodiment of the invention is a CIF130 fusion protein comprising a first protein segment and a second protein segment fused together by means of a peptide bond. The first protein segment consists of at least 17 contiguous amino acids of a human CIF130 protein as shown in SEQ ID NO:2.

Even another embodiment of the invention is a preparation of antibodies which specifically bind to a human CIF130 protein having an amino acid sequence as shown in SEQ ID NO:2.

Still another embodiment of the invention is a cDNA molecule which encodes a human CIF130 protein having an amino acid sequence which is at least 85% identical to SEQ ID NO:2. Percent identity is determined using a Smith-Waterman homology search algorithm using an affine gap search with a gap open penalty of 12 and a gap extension penalty of 1.

A further embodiment of the invention is a cDNA molecule which encodes at least 17 contiguous amino acids of SEQ ID NO:2.

Another embodiment of the invention is a cDNA molecule comprising at least 12 contiguous nucleotides of SEQ ID NO:1.

Still another embodiment of the invention is a cDNA molecule which is at least 85% identical to the nucleotide sequence shown in SEQ ID NO:1. Percent identity is determined using a Smith-Waterman homology search algorithm as implemented in a MPSRCH program using an affine gap search with a gap open penalty of 12 and a gap extension penalty of 1.

Even another embodiment of the invention is an isolated and purified subgenomic polynucleotide comprising a nucleotide sequence which hybridizes to SEQ ID NO:1 after washing with 0.2×SSC at 65° C. The nucleotide sequence encodes a CIF130 protein having the amino acid sequence of SEQ ID NO:2.

Yet another embodiment of the invention is a construct comprising a promoter and a polynucleotide segment encoding at least 17 contiguous amino acids of a human CIF130 protein as shown in SEQ ID NO:2. The polynucleotide segment is located downstream from the promoter. Transcription of the polynucleotide segment initiates at the promoter.

Even another embodiment of the invention is a host cell comprising a construct which comprises a promoter and a polynucleotide segment encoding at least 17 contiguous amino acids of a human CIF130 protein having an amino acid sequence as shown in SEQ ID NO:2.

A further embodiment of the invention provides a homologously recombinant cell. The homologously recombinant cell incorporates a new transcription initiation unit. The new transcription initiation unit comprises an exogenous regulatory sequence, an exogenous exon, and a splice donor site. The transcription initiation unit is located upstream of a coding sequence of a CIF130 gene as shown in SEQ ID NO:1. The exogenous regulatory sequence directs transcription of the coding sequence of the CIF130 gene.

Another embodiment of the invention provides a method to aid in the diagnosis or prognosis of neoplasia in a human. Expression of a first CIF130 gene in a first tissue of a human suspected of being neoplastic is compared with expression of a second CIF130 gene in a second tissue of a human which is normal. The second CIF130 gene has the coding sequence shown in SEQ ID NO:1. Decreased expression of the first CIF130 relative to expression of the second CIF130 gene indicates neoplasia in the first tissue.

Another embodiment of the invention provides a method to aid in the diagnosis or prognosis of neoplasia in a human. A first human CIF130 gene, mRNA, or protein in a first tissue suspected of being neoplastic is compared with a second human CIF130 gene, mRNA, or protein in a second tissue which is normal. The second CIF130 gene has the coding sequence shown in SEQ ID NO:1. A difference between the first and second CIF130 genes, mRNAs, or proteins indicates neoplasia in the first tissue.

Yet another embodiment of the invention provides a method to aid in detecting a genetic predisposition to neoplasia in a human. A CIF130 gene, mRNA, or protein in a fetal tissue of a human is compared with a wild-type human CIF130 gene, mRNA, or protein. The wild-type CIF130 gene has the coding sequence shown in SEQ ID NO:1. A difference between the CIF130 gene, mRNA, or protein in the fetal tissue of the human and the wild-type human CIF130 gene, mRNA, or protein indicates a genetic predisposition to neoplasia in the human.

Still another embodiment of the invention provides a method of screening test compounds for the ability to interfere with the binding of a CIF130 protein to a CIF150/hTAF$_{II}$150 protein. A test compound is contacted with at least a CIF150/hTAF$_{II}$150-binding domain of a CIF130 protein as shown in SEQ ID NO:2 and at least a CIF130-binding domain of a CIF150/hTAF$_{II}$150 protein as shown in SEQ ID NO:4. The CIF130-binding domain binds to the CIF150/hTAF$_{II}$150-binding domain in the absence of the test compound. The amount of at least one of the CIF130- or CIF150/hTAF$_{II}$150-binding domains which is bound or unbound in the presence of the test compound is determined. A test compound which decreases the amount of bound CIF130- or CIF150/hTAF$_{II}$150-binding domain or which increases the amount unbound CIF130- and CIF150/hTAF$_{II}$150-binding domains is a potential inducer of mitosis or cell cycle progression.

Another embodiment of the invention provides a method of screening test compounds for the ability to interfere with the binding of a CIF130 protein to a CIF150/hTAF$_{II}$150 protein. A cell is contacted with a test compound. The cell comprises two fusion proteins. A first fusion protein comprises (1) a CIF150/hTAF$_{II}$150-binding domain of a CIF130 protein as shown in SEQ ID NO:2 and (2) either a DNA binding domain or a transcriptional activating domain. A second fusion protein comprises a CIF130-binding domain of a CIF150/hTAF$_{II}$150 protein as shown in SEQ ID NO:4. The CIF130-binding domain binds to the CIF150/hTAF$_{II}$150-binding domain. If the first fusion protein comprises a DNA binding domain, then the second fusion protein comprises a transcriptional activating domain. If the first fusion protein comprises a transcriptional activating domain, then the second fusion protein comprises a DNA binding domain. The interaction of the first and second fusion proteins reconstitutes a sequence-specific transcription activating factor. The cell also comprises a reporter gene comprising a DNA sequence to which the DNA binding domain specifically binds. Expression of the reporter gene is measured. A test compound which decreases the expression of the reporter gene is a potential inducer of mitosis or cell cycle progression.

The present invention thus provides the art with reagents and methods of regulating mitosis or cell cycle progression of human cells and of treating disorders associated with alterations in cell cycle progression.

BRIEF DESCRIPTION OF THE DRAWINGS

FIGS. 1A–1F. FIGS. 1A–1F show nucleotide coding sequences of the CIF130 gene (SEQ ID NO:1) and translated amino acid sequences of forms of CIF130 protein. Full length CIF130 alternate start codons and a 38 basepair insert are indicated in the Figure. cDNA translate is SEQ ID NO:2.

FIGS. 2A–2B. FIGS. 2A–2B provide the DNA sequence of CIF150 (SEQ ID NO:3).

FIG. 3. FIG. 3 provides the amino acid sequence of CIF150 (SEQ ID NO:4).

DETAILED DESCRIPTION OF THE PREFERRED EMBODIMENTS

It is a discovery of the present invention that a CIF130 gene product binds to and negatively regulates CIF150/hTAF$_{II}$150 activity. CIF150/hTAF$_{II}$150 is required for a human cell to enter mitosis. Kaufmann et al., *Mol. Cell. Biol.* 18(1): 233–39 (1998). In particular, CIF150/hTAF$_{II}$150 is an essential cofactor for THF$_{II}$D-dependent transcription from promoters containing initiator elements, such as the adenovirus major late promoter. CIF150/hTAF$_{II}$150 also directly interacts with the transcription factor hTAF$_{II}$135 and stimulates cyclin A and B1 expression. A nucleotide sequence encoding CIF150/hTAF$_{II}$150 is shown in SEQ ID NO:3. The amino acid sequence of CIF150/hTAF$_{II}$150 is shown in SEQ ID NO:4.

CIF130 binds to and negatively regulates CIF150/hTAF$_{II}$150. CIF130 has sequence homology to ATP-dependent RNA helicases (DEAD-box proteins), which block entry into mitosis in Schizosaccharomyces pombe. CIF130 is implicated in promoter clearance and processing of precursor RNA, particularly in the release of spliced mRNA from the spliceosome after splicing of precursor RNA is complete. Thus, CIF130 provides a potential link between transcriptional and translational regulation of gene expression, by modifying the structure of the nascent RNA. In addition, CIF130 mRNA is differentially expressed in tumors, such as human brain, uterine, Fallopian tube, and ovarian tumors, compared to normal tissues.

CIF130 protein can exist in a number of forms. One form of CIF130 has the amino acid sequence shown in SEQ ID NO:2. Other forms can result from translation of the CIF130 gene starting at alternate start codons and/or from inclusion or omission of a 38 basepair insertion in the CIF130 mRNA (FIG. 1). Protein variants of forms of CIF130 protein are also included in the invention. Protein variants can be naturally or non-naturally occurring. Naturally occurring CIF130 variants are those which are found in humans or other species and which comprise amino acid sequences which are substantially identical to the amino acid sequence shown in SEQ ID NO:2 or to shorter forms of this amino acid sequence, as indicated in FIG. 1, with or without the 12 amino acid insert encoded by the optional 38 basepair insert. Non-naturally occurring CIF130 variants which differ by as much as, for example, four amino acids and retain substantially the same biological activities as naturally occurring CIF130 variants are also included here.

Preferably, naturally or non-naturally occurring protein variants have amino acid sequences which are at least 85%, 90%, or 95% identical to the amino acid sequence shown in SEQ ID NO:2 or to a shorter portion of SEQ ID NO:2 as shown in FIG. 1 and have similar biological properties, including the ability to bind to CIF150/hTAF$_{II}$150 and to inhibit mitosis or cell cycle progression. More preferably, the molecules are 98% or 99% identical. Percent sequence identity between a putative human CIF130 variant and the amino acid sequence of SEQ ID NO:2 or to a shorter portion of SEQ ID NO:2 as shown in FIG. 1 is determined using the Smith-Waterman homology search algorithm using an affine gap search with a gap open penalty of 12 and a gap extension penalty of 1. The Smith-Waterman homology search algorithm is taught in Smith and Waterman, *Adv. Appl. Math.* (1981) 2:482–489.

Guidance in determining which amino acid residues may be substituted, inserted, or deleted without abolishing biological or immunological activity may be found using computer programs well known in the art, such as DNASTAR software. Preferably, the amino acid changes in CIF130 variants or derivatives are conservative amino acid changes, i.e., substitutions of similarly charged or uncharged amino acids. A conservative amino acid change involves substitution of one of a family of amino acids which are related in their side chains. Naturally occurring amino acids are generally divided into four families: acidic (aspartate, glutamate), basic (lysine, arginine, histidine), non-polar (alanine, valine, leucine, isoleucine, proline, phenylalanine, methionine, tryptophan), and uncharged polar (glycine, asparagine, glutamine, cystine, serine, threonine, tyrosine) amino acids. Phenylalanine, tryptophan, and tyrosine are sometimes classified jointly as aromatic amino acids.

It is reasonable to expect that an isolated replacement of a leucine with an isoleucine or valine, an aspartate with a glutamate, a threonine with a serine, or a similar replacement of an amino acid with a structurally related amino acid will not have a major effect on the binding properties of the resulting CIF130 variant, especially if the replacement does not involve an amino acid at the CIF150/hTAF$_{II}$150 binding site of CIF130. Variants of CIF130 proteins bind to CIF150/hTAF$_{II}$150 and inhibit mitosis or cell cycle progression. Properties and functions of CIF130 variants are of the same type as a CIF130 protein having the amino acid sequence shown in SEQ ID NO:2 or a shorter version of SEQ ID NO:2 as shown in FIG. 1 although the properties and functions may differ in degree. Whether an amino acid change results in a functional CIF130 protein or polypeptide variant able to bind to CIF150/hTAF$_{11}$150 and inhibit mitosis or cell cycle progression can readily be determined using, for example, in vitro DNA binding assays, as taught in Kaufmann & Smale, 1994, *Genes Devel.* 8:821–29 and Kaufmann et al., 1996, *Genes Devel.* 10:873–86, or by assaying the ability of the CIF130 protein or polypeptide variant to inhibit cell cycle progression, as described below.

CIF130 polypeptides or polypeptide variants differ in length from natural CIF130 polypeptides and contain 6, 7, 8, 9, 10, 11, 12, 13, 14, 15, 16, 17, 18, 19, 20, 25, 30, 35, 40, 45, 50, 75, 100, 200, 300, 400, 500, 600, 700, 800, 900, or 1000 or more amino acids of a CIF130 protein or variant in the same primary order as found in a CIF130 protein or variant obtained from a natural source. Polypeptide molecules having substantially the same amino acid sequence as CIF130 but possessing minor amino acid substitutions which do not substantially affect the ability of the CIF130 polypeptide variants to interact with CIF130-specific molecules, such as CIF150/hTAF$_{11}$150 or antibodies which specifically bind to CIF130, are within the definition of CIF130. CIF130 variants include glycosylated forms, aggregative conjugates with other molecules, and covalent conjugates with unrelated chemical moieties.

CIF130 variants of the invention also include allelic variants, species variants, and muteins. Truncations or deletions of regions which do not affect the properties or functions of CIF130 described above are also variants of CIF130. Covalent variants can be prepared by linkage of functionalities to groups which are found in the amino acid chain or at the N- or C-terminal residue, as is known in the art.

A subset of mutants, called muteins, is a group of polypeptides with the non-disulfide bond participating cysteines substituted with a neutral amino acid, generally, with serines. These mutants may be stable over a broader temperature range than CIF130. See Mark et al., U.S. Pat. No. 4,959,314.

Naturally occurring CIF130 proteins or polypeptides can be purified from human cells or cell lines, such as HeLa or NTH 3T3 cells, by methods known in the art. CIF130 copurifies with CIF150/hTAF$_{11}$150; thus, the initial purification steps for each protein are the same. Preferably, CIF130 is purified from HeLa cell extracts (Dignam et al., 1983, *Nucl. Acids Res.* 11:1475–89) by Ni affinity chromatography, as described in Example 1. Purified CIF150/hTAF$_{II}$150 and CIF130 proteins can be visualized by sodium dodecyl sulfate-6% polyacrylamide gel electrophoresis, followed by silver staining. CIF130 can be separated from CIF150/hTAF$_{II}$150 by excising the CIF130-containing band from the SDS gel and eluting the CIF130 protein, as is known in the art. A preparation of isolated and purified CIF130 protein is at least 80% pure; preferably, the preparations are 90%, 95%, or 99% pure.

CIF130 proteins and polypeptides can also be produced by recombinant DNA methods or by synthetic chemical methods. For production of recombinant CIF130 proteins or polypeptides, coding sequences selected from the CIF130 nucleotide sequence shown in SEQ ID NO:1 can be expressed in known prokaryotic or eukaryotic expression systems (see below). To avoid non-specific T7 RNA polymerase transcription in functional assays, in vitro translated CIF130 can be purified with Ni-NTA-agarose as described above (100 mM imidazole eluate) and concentrated with a Centricon 30 concentrator (Amicon). Bacterial, yeast, insect, or mammalian expression systems can be used, as is known in the art. Alternatively, synthetic chemical methods, such as solid phase peptide synthesis, can be used to synthesize CIF130 protein or polypeptides. CIF130 variants can be similarly produced.

Fusion proteins comprising at least 6, 7, 8, 9, 10, 11, 12, 13, 14, 15, 16, 17, 20, 25, 30, 35, 40, 45, 50, 75, 100, 200, 300, 400, 500, 600, 700, 800, 900, or 1000 or more contiguous CIF130 amino acids can also be constructed. Human CIF130 fusion proteins are useful for generating antibodies against CIF130 amino acid sequences and for use in various assay systems. For example, CIF130 fusion proteins can be used to identify proteins which interact with CIF130 protein and influence its function. Physical methods, such as protein affinity chromatography, or library-based assays for protein-protein interactions, such as the yeast two-hybrid or phage display systems, can also be used for this purpose. Such methods are well known in the art and can also be used as drug screens, as described below.

A CIF130 fusion protein comprises two protein segments fused together by means of a peptide bond. The first protein segment comprises at least 6, 7, 8, 9, 10, 11, 12, 13, 14, 15, 16, 17, 20, 25, 30, 35, 40, 50, 75, 75, 100, 200, 300, 400, 500, 600, 700, 800, 900, or 1000 or more contiguous amino acids of a CIF130 protein. The amino acids can be selected from the amino acid sequence shown in SEQ ID NO:2 or from a biologically active variant of that sequence, such as those described above. The first protein segment can also comprise a full-length CIF130 protein as shown in SEQ ID NO:2 or an alternate form of CIF130 as shown in FIG. 1. The first protein segment can be N-terminal or C-terminal, as is convenient.

The second protein segment can be a full-length protein or a protein fragment or polypeptide. Proteins commonly used in fusion protein construction include β-galactosidase, β-glucuronidase, green fluorescent protein (GFP), autofluorescent proteins, including blue fluorescent protein (BFP), glutathione-S-transferase (GST), luciferase, horseradish peroxidase (HRP), and chloramphenicol acetyltransferase (CAT). Epitope tags can be used in fusion protein constructions, including histidine (His) tags, FLAG tags, influenza hemagglutinin (HA) tags, Myc tags, VSV-G tags, and thioredoxin (Trx) tags. Other fusion constructions can include maltose binding protein (MBP), S-tag, Lex A DNA binding domain (DBD) fusions, GAL4 DNA binding domain fusions, and herpes simplex virus (HSV) BP16 protein fusions.

CIF130 fusion proteins can be made by covalently linking the first and second protein segments or by standard procedures in the art of molecular biology. Recombinant DNA methods can be used to prepare CIF130 fusion proteins, for example, by making a DNA construct which comprises coding sequences selected from SEQ ID NO:1 in proper reading frame with nucleotides encoding the second protein segment and expressing the DNA construct in a host cell, as is known in the art. Many kits for constructing fusion proteins are available from companies which supply research labs with tools for experiments, including, for example, Promega Corporation (Madison, Wisc.), Stratagene (La Jolla, Calif.). Clontech (Mountain View, Calif.), Santa Cruz Biotechnology (Santa Cruz, Calif.), MBL International Corporation (MIC; Watertown, Mass.), and Quantum Biotechnologies (Montreal, Canada; 1-888-DNA-KITS).

Isolated and purified CIF130 proteins, polypeptides, variants, or fusion proteins can be used as immunogens, to obtain a preparation of antibodies which specifically bind to a CIF130 protein. The antibodies can be used, inter alia, to detect wild-type CIF130 proteins in human tissue and fractions thereof The antibodies can also be used to detect the presence of mutations in the CIF130 gene which result in under- or overexpression of the CIF130 protein or in expression of a CIF130 protein with altered size or electrophoretic mobility.

Antibodies which specifically bind to epitopes of CF130 proteins, polypeptides, fusion proteins, or biologically active variants can be used in immunochemical assays, including but not limited to Western blots, ELISAs, radioimmunoassays, immunohistochemical assays, immunoprecipitations, or other immunochemical assays known in the art. Typically, antibodies of the invention provide a detection signal at least 5-, 10-, or 20-fold higher than a detection signal provided with other proteins when used in such immunochemical assays. Preferably, antibodies which specifically bind to CIF130 epitopes do not detect other proteins in immunochemical assays and can immunoprecipitate CIF130 protein or polypeptides from solution.

CIF130-specific antibodies specifically bind to epitopes present in a CIF130 protein having the amino acid sequence shown in SEQ ID NO:2 or to biologically active variants of that sequence. Typically, at least 6, 8, 10, or 12 contiguous amino acids are required to form an epitope. However, epitopes which involve non-contiguous amino acids may require more, e.g., at least 15, 25, or 50 amino acids. Preferably, CIF130 epitopes are not present in other human proteins.

Epitopes of CIF130 which are particularly antigenic can be selected, for example, by routine screening of CIF130 polypeptides for antigenicity or by applying a theoretical method for selecting antigenic regions of a protein to the amino acid sequence shown in SEQ ID NO:2. Such methods are taught, for example, in Hopp and Wood, *Proc. Nail. Acad. Sci. U.S.A.* 78, 3824–28 (1981), Hopp and Wood, *Mol. Immunol.* 20, 483–89 (1983), and Sutcliffe et al., *Science* 219, 660–66 (1983).

Any type of antibody known in the art can be generated to bind specifically to CIF130 epitopes. For example, preparations of polyclonal and monoclonal antibodies can be made using standard methods which are well known in the art. Similarly, single-chain antibodies can also be prepared. Single-chain antibodies which specifically bind to CIF130 epitopes can be isolated, for example, from single-chain immunoglobulin display libraries, as is known in the art. The library is "panned" against CIF130 amino acid sequences, and a number of single chain antibodies which bind with high-affinity to different epitopes of CIF130 protein can be isolated. Hayashi et al., 1995, *Gene* 160:129–30. Single-chain antibodies can also be constructed using a DNA amplification method, such as the polymerase chain reaction (PCR), using hybridoma cDNA as a template. Thirion et al., 1996, *Eur. J Cancer Prev.* 5:507–11.

Single-chain antibodies can be mono- or bispecific, and can be bivalent or tetravalent. Construction of tetravalent, bispecific single-chain antibodies is taught, for example, in Coloma and Morrison, 1997, *Nat. Biotechnol.* 15:159–63. Construction of bivalent, bispecific single-chain antibodies is taught inter alia in Mallender and Voss, 1994, *J Biol. Chem.* 269:199–206.

A nucleotide sequence encoding a single-chain antibody can be constructed using manual or automated nucleotide synthesis, cloned into an expression construct using standard recombinant DNA methods, and introduced into a cell to express the coding sequence, as described below. Alternatively, single-chain antibodies can be produced directly using, for example, filamentous phage technology. Verhaar et al., 1995, *Int. J. Cancer* 61:497–501; Nicholls et al., 1993, *J. Immunol. Meth.* 165:81–91.

Monoclonal and other antibodies can also be "humanized" in order to prevent a patient from mounting an immune response against the antibody when it is used therapeutically. Such antibodies may be sufficiently similar in sequence to human antibodies to be used directly in therapy or may require alteration of a few key residues. Sequence differences between, for example, rodent antibodies and human sequences can be minimized by replacing residues which differ from those in the human sequences, for example, by site directed mutagenesis of individual residues, or by grafting of entire complementarity determining regions. Alternatively, one can produce humanized antibodies using recombinant methods, as described in GB2188638B. Antibodies which specifically bind to CIF130 epitopes can contain antigen binding sites which are either partially or fully humanized, as disclosed in U.S. Pat. No. 5,565,332.

Other types of antibodies can be constructed and used in methods of the invention. For example, chimeric antibodies can be constructed as disclosed, for example, in WO 93/03151. Binding proteins which are derived from immunoglobulins and which are multivalent and multispecific, such as the "diabodies" described in WO 94/13804, can also be prepared.

Antibodies of the invention can be purified by methods well known in the art. For example, antibodies can be affinity purified by passing the antibodies over a column to which a CIF130 protein, polypeptide, biologically active variant, or fusion protein is bound. The bound antibodies can then be eluted from the column, using a buffer with a high salt concentration.

CIF130-specific binding polypeptides other than antibodies can also be generated. CIF130-specific binding polypeptides are polypeptides which bind with CIF130 or its variants and which have a measurably higher binding affinity for CIF130 and polypeptide derivatives of CIF130 than for other polypeptides tested for binding. Higher affinity by a factor of 10 is preferred, more preferably a factor of 100. Such polypeptides can be found, for example, using the yeast two-hybrid system.

SEQ ID NO:1 represents a coding sequence of CIF130. Other forms of CIF130 are encoded by portions of SEQ ID NO:1, utilizing any of the start codons indicated in FIG. 1.

The 38 basepair insertion indicated in FIG. 1 can be included or not, to form alternatively spliced forms of CIF130 mRNA and protein. The complement of the nucleotide sequence shown in SEQ ID NO:1 consists of a contiguous nucleotide sequence which forms Watson-Crick base pairs with the contiguous nucleotide sequences shown in SEQ ID NO:1 and in FIG. 1.

Subgenomic CIF130 polynucleotides contain less than a whole chromosome. Preferably, the polynucleotides are intron-free. Purified and isolated CIF130 subgenomic polynucleotides can comprise at least 6, 10, 11, 12, 13, 14, 15, 16, 17, 18, 19,20,25, 30, 35, 40, 45, 50, 75, 100, 125, 150, 175, 200, 250, 300, 350, 400, 450, 500, 550, 600, 650, 700, 750, 775, 780, 787, 788, 789, 800, 850, 900, 950, 1000, 1100,, 1187, 1188, 1189, 1190, 1191, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3350, 3351, 3352, 3400, 3500, 3600, 3700, or 3800 or more contiguous nucleotides selected from SEQ ID NO:1 or the coding sequences shown in FIG. 1 or their complements.

Antisense oligonucleotides, primers, and probes of the invention can consist of at least 11, 12, 15, 20, 25, 30, 50, or 100 contiguous nucleotides which are complementary to the coding sequences shown in SEQ ID NO:1 and FIG. 1. A complement of the entire coding sequence can also be used. Double-stranded subgenomic polynucleotides which comprise all or a portion of the nucleotide sequence shown in SEQ ID NO:1, as well as polynucleotides which encode CIF130-specific antibodies or ribozymes, are also subgenomic polynucleotides of the invention.

Degenerate nucleotide sequences encoding amino acid sequences of CIF130 protein or biologically active CIF130 variants as well as homologous nucleotide sequences which are at least 65%, 75%, 85%, 90%, 95%, 96%, 97%, 98%, or 99% identical to the nucleotide sequence shown in SEQ ID NO:1, are also CIF130 polynucleotides. Percent sequence identity between a polynucleotide having a nucleotide sequence selected from SEQ ID NO:1 or the coding sequences shown in FIG. 1 and a putative homologous or degenerate CIF130 nucleotide sequence is determined using computer programs which employ the Smith-Waterman algorithm, for example as implemented in the MPSRCH program (Oxford Molecular), using an affine gap search with the following parameters: a gap open penalty of 12 and a gap extension penalty of 1.

Nucleotide sequences which hybridize to a coding sequence shown in SEQ ID NO:1 or FIG. 1 or their complements with at most 1, 2, 3, 4, 5, 10, 15, 20, 25, 30, or 35% basepair mismatches are also CIF130 subgenomic polynucleotides of the invention. For example, using the following wash conditions—2xSSC (0.3 M sodium chloride, 0.03 M sodium citrate, pH 7.0), 0.1% SDS, room temperature twice, 30 minutes each; then 2xSSC, 0.1% SDS, 50° C. once, 30 minutes; then 2xSSC, room temperature twice, 10 minutes each—homologous CIF130 sequences can be identified which contain at most about 25–30% basepair mismatches with a coding sequence of SEQ ID NO:1 or its complement. More preferably, homologous nucleic acid strands contain 15–25% basepair mismatches, even more preferably 5–15% basepair mismatches.

It is well known that the $T_m$ of a double-stranded DNA decreases by 1–1.5° C. with every 1% decrease in homology (Bonner et al., *J. Mol. Biol.* 81, 123 (1973). Homologous CIF130 polynucleotides can therefore be identified, for example, by hybridizing a putative homologous CIF130 polynucleotide with a polynucleotide having a coding sequence selected from SEQ ID NO:1 or the coding sequences shown in FIG. 1, comparing the melting temperature of the test hybrid with the melting temperature of a hybrid comprising a polynucleotide having the coding sequence selected from SEQ ID NO:1 or the coding sequences shown in FIG. 1 and a polynucleotide which is perfectly complementary to the coding sequence, and calculating the number of basepair mismatches within the test hybrid.

Nucleotide sequences which hybridize to coding sequences shown in SEQ ID NO:1 or FIG. 1 or their complements following stringent hybridization and/or wash conditions are also CIF130 subgenomic polynucleotides of the invention. Stringent wash conditions are well known and understood in the art and are disclosed, for example, in Sambrook et al., MOLECULAR CLONING: A LABORATORY MANUAL, 2d ed., 1989, at pages 9.50–9.51.

Typically, for stringent hybridization conditions a combination of temperature and salt concentration should be chosen that is approximately 12–20° C. below the calculated $T_m$ of the hybrid under study. The $T_m$ of a hybrid between the CIF130 sequence shown in SEQ ID NO:1 and a polynucleotide sequence which is 65%, 75%, 85%, 90%, 95%, 96%, 97%, 98%, or 99% identical to SEQ ID NO:1 can be calculated, for example, using the equation of Bolton and McCarthy, *Proc. Natl. Acad. Sci. U.S.A.* 48, 1390 (1962):

$T_m = 81.5°$ C. $- 16.6(\log_{10}[\text{Na}^-]) + 0.41(\%G+C) - 0.63$ (%formamide) $- 600/l$, where l=the length of the hybrid in basepairs.

Stringent wash conditions include, for example, 4xSSC at 65° C., or 50% formamide, 4xSSC at 42° C., or 0.5xSSC, 0.1% SDS at 65° C. Highly stringent wash conditions include, for example, 0.2xSSC at 65° C.

CIF130 subgenomic polynucleotides can be isolated and purified free from other nucleotide sequences using standard nucleic acid purification techniques. For example, restriction enzymes and probes can be used to isolate subgenomic polynucleotide fragments which comprise the CIF130 coding sequences. Isolated and purified subgenomic polynucleotides are in preparations which are free or at least 90% free of other molecules.

Complementary DNA (cDNA) molecules which encode CIF130 proteins are also CIF130 subgenomic polynucleotides of the invention. CIF130 cDNA molecules can be made with standard molecular biology techniques, using CIF130 mRNA as a template. CIF130 cDNA molecules can thereafter be replicated using molecular biology techniques known in the art and disclosed in manuals such as Sambrook et al., 1989. An amplification technique, such as the polymerase chain reaction (PCR), can be used to obtain additional copies of subgenomic polynucleotides of the invention, using either human genomic DNA or cDNA as a template.

Alternatively, synthetic chemistry techniques can be used to synthesize CIF130 subgenomic polynucleotide molecules of the invention. The degeneracy of the genetic code allows alternate nucleotide sequences to be synthesized which will encode a CIF130 protein having the amino acid sequence shown in SEQ ID NO:2 or an alternate form of CIF130 as shown in FIG. 1 or a biologically active variant of one of those sequences. All such nucleotide sequences are within the scope of the present invention.

The invention also provides polynucleotide probes which can be used to detect CIF130 sequences, for example, in hybridization protocols such as Northern or Southern blotting or in situ hybridizations. Polynucleotide probes of the invention comprise at least 12, 13, 14, 15, 16, 17, 18, 19, 20, 30, or 40 or more contiguous nucleotides selected from SEQ ID NO:1 or a coding sequence shown in FIG. 1. Polynucleotide probes of the invention can comprise a detectable label, such as a radioisotopic, fluorescent, enzymatic, or chemiluminescent label.

Purified and isolated CIF130 subgenomic polynucleotides can be used, inter alia, as primers to obtain additional copies of the polynucleotides, to express human CIF130 mRNA, protein, polypeptides, or fusion proteins, as probes for identifying wild-type and mutant CIF130 protein coding sequences, and to generate CIF130 antisense oligonucleotides and ribozymes. For example, a CIF130 subgenomic polynucleotide comprising CIF130 coding sequences can be used in an expression construct, to express all or a portion of a CIF130 protein in a host cell. Host cells comprising CIF130 expression constructs can be prokaryotic or eukaryotic. Preferably, the CIF130 subgenomic polynucleotide is inserted into an expression plasmid (for example, the Ecdyson system, pIND, In Vitro Gene).

A variety of host cells are available for use in bacterial, yeast, insect, and human expression systems and can be used to express CIF130 expression constructs (see below). Expression constructs of the invention can be introduced into host cells using any technique known in the art. These techniques include transferrin-polycation-mediated DNA. transfer, transfection with naked or encapsulated nucleic acids, liposome-mediated cellular fusion, intracellular transportation of DNA-coated latex beads, protoplast fusion, viral infection, electroporation, and calcium phosphate-mediated transfection.

A CIF130 expression construct comprises a promoter which is functional in the particular host cell selected. The skilled artisan can readily select an appropriate promoter from the large number of cell type-specific promoters known and used in the art. The expression construct can also contain a transcription terminator which is functional in the host cell. The expression construct comprises a polynucleotide segment which encodes all or a portion of a CIF130 protein, variant, fusion protein, antibody, or ribozyme. The polynucleotide segment is located downstream from the promoter. Transcription of the polynucleotide segment initiates at the promoter. The expression construct can be linear or circular and can contain sequences, if desired, for autonomous replication.

CIF130 subgenomic polynucleotides can be propagated in vectors and cell lines using techniques well known in the art. CIF130 subgenomic polynucleotides can be on linear or circular molecules. They can be on autonomously replicating molecules or on molecules without replication sequences. They can be regulated by their own or by other regulatory sequences, as are known in the art.

Bacterial systems for expressing CIF130 subgenomic polynucleotides include those described in Chang et al., *Nature* (1978) 275: 615, Goeddel et al., *Nature* (1979) 281: 544, Goeddel et al., *Nucleic Acids Res.* (1980) 8 4057, EP 36,776, U.S. Pat. No. 4,551,433, deBoer et al., *Proc. Natl. Acad Sci. USA* (1983) 80: 21–25, and Siebenlist et al., *Cell* (1980) 20: 269.

Expression systems in yeast include those described in Hinnen et al., *Proc. Natl. Acad. Sci. USA* (1978) 75: 1929; Ito et al., *J. Bacteriol.* (1983) 153: 163; Kurtz et al., *Mol. Cell. Biol.* (1986) 6: 142; Kunze et al., *J Basic Microbiol.* (1985) 25: 141; Gleeson et al., *J. Gen. Microbiol.* (1986) 132: 3459, Roggenkamp et al., *Mol. Gen Genet.* (1986) 202:302) Das et al., *J. Bacteriol.* (1984) 158: 1165; De Louvencourt et al., *J. Bacteriol.* (1983) 154: 737, Van den Berg et al., *Bio/Technology* (1990) 8: 135; Kunze et al., *J Basic Microbiol.* (1985) 25: 141; Cregg et al., *Mol. Cell. Biol.* (1985) 5: 3376, U.S. Pat. No. 4,837,148, U.S. Pat. No. 4,929,555; Beach and Nurse, *Nature* (1981) 300: 706; Davidow et al, *Curr. Genet.* (1985) 10: 380, Gaillardin et al., *Curr. Genet.* (1985) 10: 49, Ballance et al., *Biochem. Biophys. Res. Commun.* (1983) 112: 284–289; Tilburn et a., *Gene* (1983) 26: 205–221, Yelton et al., *Proc. Natl. Acad Sci. USA* (1984) 81: 1470–1474, Kelly and Hynes, *EMBO J.* (1985) 4: 475479; EP 244,234, and WO 91/00357.

Expression of CIF130 subgenomic polynucleotides in insects can be carried out as described in U.S. Pat. No. 4,745,051, Friesen et al (1986) "The Regulation of Baculovirus Gene Expression" in: The Molecular Biology of Baculoviruses (W. Doerfler, ed.), EP 127,839, EP 155,476, and Vlak et al., *J. Gen. Virol.* (1988) 69: 765–776, Miller et al., *Ann. Rev. Microbiol.* (1988) 42: 177, Carbonell et al., *Gene* (1988) 73: 409, Maeda et al., *Nature* (1985) 315: 592–594, Lebacq-Verheyden et al., *Mol. Cell. Biol.* (1988) 8: 3129; Smith et al., *Proc. Natl Acad Sci. USA* (1985) 82: 8404, Miyajima et al, *Gene* (1987) 58: 273; and Martin et al., *DNA* (1988) 7:99. Numerous baculoviral strains and variants and corresponding permissive insect host cells from hosts are described in Luckow et al., *Bio/Technlology* (1988) 6: 47–55, Miller et al., in Genetic Engineering (Setlow, J. K. et al. eds.), Vol. 8 (Plenum Publishing, 1986), pp. 277–279, and Maeda et al., *Nature*, (1985) 315: 592–594.

Mammalian expression of CIF130 subgenomic polynucleotides can be achieved as described in Dijkema et al., *EMBO J* (1985) 4: 761, Gorman et al, *Proc. Natl. Acad Sci. USA* (1982b) 79: 6777, Boshart et al., *Cell* (1985) 41: 521 and U.S. Pat. No. 4,399,216. Other features of mammalian expression can be facilitated as described in Ham and Wallace, *Meth. Enz.* (1979) 58: 44, Barnes and Sato, *Anal. Biochem.* (1980) 102: 255, U.S. Pat. No. 4,767,704, U.S. Pat. No. 4,657,866, U.S. Pat. No. 4,927,762, U.S. Pat. No. 4,560,655, WO 90/103430, WO 87/00195, and U.S. Pat. No. RE 30,985.

Polynucleotides of the invention can also be used in gene delivery vehicles, for the purpose of delivering a CIF130 mRNA or oligonucleotide (either with the sequence of native CIF130 mRNA or its complement), fiull-length CIF130 protein, CIF130 fusion protein, CIF130 polypeptide, or CIF130-specific ribozyme or single-chain antibody, into a cell preferably a eukaryotic cell. According to the present invention, a gene delivery vehicle can be, for example, naked plasmid DNA, a viral expression vector comprising a CIF130 polynucleotide, or a CIF130 polynucleotide in conjunction with a liposome or a condensing agent.

In one embodiment of the invention, the gene delivery vehicle comprises a promoter and a CIF130 polynucleotide. Preferred promoters are tissue-specific promoters and promoters which are activated by cellular proliferation, such as the thymidine kinase and thymidylate synthase promoters. Other preferred promoters include promoters which are activatable by infection with a virus, such as the α- and β-interferon promoters, and promoters which are activatable by a hormone, such as estrogen. Other promoters which can be used include the Moloney virus LTR, the CMV promoter, and the mouse albumin promoter.

A CIF130 gene delivery vehicle can comprise viral sequences such as a viral origin of replication or packaging signal. These viral sequences can be selected from viruses such as astrovirus, coronavirus, orthomyxovirus, papovavirus, paramyxovirus, parvovirus, picomavirus, poxvirus, retrovirus, togavirus or adenovirus. In a preferred embodiment, the CIF130 gene delivery vehicle is a recombinant retroviral vector. Recombinant retroviruses and various uses thereof have been described in numerous references including, for example, Mann et al., *Cell* 33:153, 1983, Cane and Mulligan, *Proc. Natl. Acad Sci. USA* 81:6349, 1984, Miller et al., *Human Gene Therapy* 1:5–14, 1990, U.S. Pat. Nos. 4,405,712, 4,861,719, and 4,980,289, and PCT Application Nos. WO 89/02,468, WO 89/05,349, and WO 90/02,806. Numerous retroviral gene delivery vehicles can be utilized in the present invention, including for example those described in EP 0,415,731, WO 90/07936, WO 94/03622; WO 93/25698; WO 93/25234, U.S. Pat. No. 5,219,740; WO 9311230; WO 9310218; Vile and Hart, *Cancer Res.* 53:3860–3864, 1993; Vile and Hart, *Cancer Res.* 53:962–967, 1993; Ram et al., *Cancer Res.* 53:83–88, 1993; Takamiya et al., *J. Neurosci. Res.* 33:493–503, 1992; Baba et al., *J. Neurosurg.* 79:729–735, 1993 (U.S. Pat. No. 4,777,127, GB 2,200,651, EP 0,345,242 and WO91/02805).

Packaging cell lines suitable for use with the above-described retroviral gene delivery vehicles can be readily prepared (see Ser. No. 08/240,030, filed May 9, 1994; see also WO 92/05266) and used to create producer cell lines (also termed vector cell lines or "VCLs") for production of recombinant viral particles A CIF130 gene delivery vehicle can also be a recombinant adenoviral gene delivery vehicle. Such vehicles can be readily prepared and utilized given the disclosure provided herein (see Berkner, *Biotechniques* 6:616, 1988, and Rosenfeld et al., *Science* 252:431, 1991, WO 93/07283, WO 93/06223, and WO 93/07282). Adeno-associated viral CIF130 gene delivery vehicles can also be constructed and used to deliver CIF130 amino acids or nucleotides. The use of adeno-associated viral gene delivery vehicles in vitro is described in Chatterjee et al., *Science* 258: 1485–1488 (1992), Walsh et al., *Proc. Nat'l. Acad Sci.* 89: 7257–7261 (1992), Walsh et al., *J. Clin. Invest.* 94: 1440–1448 (1994), Flotte et al., *J. Biol. Chem.* 268: 3781–3790 (1993), Ponnazhagan et al., *J. Exp. Med.* 179: 733–738 (1994), Miller et al., *Proc. Nat'l Acad. Sci.* 91: 10183–10187 (1994), Einerhand et al., *Gene Ther.* 2: 336–343 (1995), Luo et al, *Exp. Hematol.* 23: 1261–1267 (1995), and Zhou et al., *Gene Therapy* 3: 223–229 (1996). In vivo use of these vehicles is described in Flotte et al., *Proc. Nat'l Acad Sci.* 90: 10613–10617 (1993), and Kaplitt et al., *Nature Genet.* 8:148–153 (1994).

In another embodiment of the invention, a CIF130 gene delivery vehicle is derived from a togavirus. Preferred togaviruses include alphaviruses, in particular those described in U.S. Ser. No. 08/405,627, filed Mar. 15, 1995, WO 95/07994. Alpha viruses, including Sindbis and ELVS viruses can be gene delivery vehicles for CIF130 polynucleotides. Alpha viruses are described in WO 94/21792, WO 92/10578 and WO 95/07994. Several different alphavirus gene delivery vehicle systems can be constructed and used to deliver CIF130 polynucleotides to a cell according to the present invention. Representative examples of such systems include those described in U.S. Pat. Nos. 5,091,309 and 5,217,879. Particularly preferred alphavirus gene delivery vehicles for use in the present invention include those which are described in WO 95/07994, and U.S. Ser. No. 08/405,627.

A CIF130 polynucleotide of the invention can also be combined with a condensing agent to form a gene delivery vehicle. In a preferred embodiment, the condensing agent is a polycation, such as polylysine, polyarginine, polyornithine, protamine, spermine, spermidine, and putrescine. Many suitable methods for making such linkages are known in the art (see, for example, Ser. No. 08/366,787, filed Dec. 30, 1994).

In an alternative embodiment, a CIF130 polynucleotide is associated with a liposome to form a gene delivery vehicle. See Stryer, *Biochemistry*, pp. 236–240, 1975 (W.H. Freeman, San Francisco, Calif.), Szoka et al., *Biochim. Biophys. Acta* 600:1, 1980; Bayer et al., *Biochim. Biophys. Acta.* 550:464, 1979; Rivnay et al., *Meth. Enzymol.* 149:119, 1987; Wang et al., *Proc. Natl. Acad Sci. U.S.A.* 84: 7851, 1987, Plant et al., *Anal. Biochem.* 176:420, 1989, and U.S. Pat. No. 4,762,915. Liposomes can encapsulate a variety of nucleic acid molecules including DNA, RNA, plasmids, and expression constructs comprising CIF130 polynucleotides such those disclosed in the present invention.

In addition, lipoproteins can be included with a CIF130 polynucleotide for delivery to a cell. Examples of such lipoproteins include chylomicrons, HDL, IDL, LDL, and VLDL. Mutants, fragments, or fusions of these proteins can also be used. Modifications of naturally occurring lipoproteins can also be used, such as acetylated LDL. These lipoproteins can target the delivery of polynucleotides to cells expressing lipoprotein receptors. Preferably, if lipoproteins are included with a polynucleotide, no other targeting ligand is included in the composition.

In another embodiment, naked CIF130 polynucleotide molecules are used as gene delivery vehicles, as described in WO 90/11092 and U.S. Pat. No. 5,580,859. Such gene delivery vehicles can be either CIF130 DNA or RNA and, in certain embodiments, are linked to killed adenovirus. Curiel et al., *Hum. Gene. Ther.* 3:147–154, 1992. Other suitable vehicles include DNA-ligand (Wu et al., *J. Biol. Chem.* 264:16985–16987, 1989), lipid-DNA combinations (Felgner et al., *Proc. Nail. Acad. Sci. USA* 84:7413 7417, 1989), liposomes (Wang et al., *Proc. Natl. Acad. Sci.* 84:7851–7855, 1987) and microprojectiles (Williams et al., *Proc. Natl. Acad Sci.* 88:2726–2730, 1991).

The invention provides compositions for regulating cell cycle progression, in order to alter spatial or temporal patterns of division of a human cell. CIF130 binds to CIF150/hTAF$_{II}$150 and inhibits cell cycle progression, indicating that CIF130 negatively regulates CIF150/hTAF$_{II}$150 activity. CIF150/hTAF$_{II}$150 is required for a cell to enter mitosis. Thus, mitosis or cell cycle progression can be induced or increased by increasing expression of a human CIF130 gene. Increased CIF130 gene expression can be used to expand cell populations in vitro or for treating disorders such as anemia, which are characterized by lowered rates of mitosis. Cells in which expression of a CIF130 gene has been decreased can also be used to identify genes whose expression is dependent on a CIF130 protein. Decreased CIF130 gene expression can be used to treat conditions characterized by high rates of mitosis, such as neoplasia, metastasis of neoplasms, benign proliferative diseases, and dysplastic and hyperplastic disorders.

In one embodiment of the invention, expression of a CIF130 gene is decreased using a ribozyme, an RNA molecule with catalytic activity. See, e.g., Cech, 1987, *Science* 236: 1532–1539, Cech, 1990, *Ann. Rev. Biochem.* 59:543–568; Cech, 1992, *Curr. Opin. Struct. Biol.* 2: 605–609; Couture and Stinchcomb, 1996, *Trends Genet.* 12: 510–515. Ribozymes can be used to inhibit gene function by cleaving an RNA sequence, as is known in the art (e.g., Haseloffet al., U.S. Pat. No. 5,641,673).

The coding sequence of the CIF130 gene can be used to generate ribozymes which will specifically bind to mRNA transcribed from a CIF130 gene. Methods of designing and constructing ribozymes which can cleave other RNA molecules in trans in a highly sequence specific manner have been developed and described in the art (see Haseloff et al. (1988), *Nature* 334:585–591). For example, the cleavage activity of ribozymes can be targeted to specific CIF130 RNAs by engineering a discrete "hybridization" region into the ribozyme. The hybridization region contains a sequence complementary to the target CIF130 RNA and thus specifically hybridizes with the target (see, for example, Gerlach et al., EP 321,201). The nucleotide sequence shown in SEQ ID NO:1 provides a source of suitable hybridization region sequences. Longer complementary sequences can be used to increase the affinity of the hybridization sequence for the target. The hybridizing and cleavage regions of the CIF130 ribozyme can be integrally related; thus, upon hybridizing to the target CIF130 RNA through the complementary regions, the catalytic region of the ribozyme can cleave the target.

CIF130 ribozymes can be introduced into cells as part of a DNA construct, as is known in the art and described above. Mechanical methods, such as microinjection, liposome-mediated transfection, electroporation, or calcium phosphate precipitation, can be used to introduce the ribozyme-containing DNA construct into cells in which it is desired to decrease CIF130 expression, as described above. Alternatively, if it is desired that the cells stably retain the DNA construct, it can be supplied on a plasmid and maintained as a separate element or integrated into the genome of the cells, as is known in the art. The DNA construct can include transcriptional regulatory elements, such as a promoter element, an enhancer or UAS element, and a transcriptional terminator signal, for controlling transcription of CIF130 ribozymes in the cells.

As taught in Haseloff et al., U.S. Pat. No. 5,641,673, CIF130 ribozymes can be engineered so that ribozyme expression will occur in response to factors which induce expression of the CIF130 gene. Ribozymes can also be engineered to provide an additional level of regulation, so that destruction of CIF130 mRNA occurs only when both a CIF130 ribozyme and a CIF130 gene are induced in the cells.

In another embodiment of the invention, expression of the CIF130 gene is altered using an antisense oligonucleotide sequence. The antisense sequence is complementary to at least a portion of the coding sequence of a CIF130 gene having the nucleotide sequence shown in SEQ ID NO:1. Preferably, the antisense oligonucleotide sequence is at least six nucleotides in length, but can be about 8, 9, 10, 11, 12, 15, 20, 25, 30, 35, 40, 45, or 50 nucleotides long. Longer sequences can also be used. CIF130 antisense oligonucleotide molecules can be provided in a DNA construct and introduced into cells as described above to decrease CIF130 expression.

CIF130 antisense oligonucleotides can be deoxyribonucleotides, ribonucleotides, or a combination of both. Oligonucleotides can be synthesized manually or by an automated synthesizer, by covalently linking the 5' end of one nucleotide with the 3' end of another nucleotide with non-phosphodiester internucleotide linkages such as alkylphosphonates, phosphorothioates, phosphorodithioates, alkylphosphonothioates, alkylphosphonates, phosphoramidates, phosphate esters, carbamates, acetamidate, carboxymethyl esters, carbonates, and phosphate triesters. See Brown, 1994, *Meth. Mol. Biol.* 20:1–8; Sonveaux, 1994, *Meth. Mol. Biol.* 26:1–72; Uhlmann et al., 1990, *Chem. Rev.* 90:543–583.

Precise complementarity is not required for successful duplex formation between an antisense molecule and the complementary coding sequence of a CIF130 gene. Antisense molecules which comprise, for example, 2, 3, 4, or 5 or more stretches of contiguous nucleotides which are precisely complementary to a CIF130 coding sequence, each separated by a stretch of contiguous nucleotides which are not complementary to adjacent CIF130 coding sequences, can provide targeting specificity for CIF130 mRNA. Preferably, each stretch of contiguous nucleotides is at least 4, 5, 6, 7, or 8 or more nucleotides in length. Non-complementary intervening sequences are preferably 1, 2, 3, or 4 nucleotides in length. One skilled in the art can easily use the calculated melting point of an antisense-sense pair to determine the degree of mismatching which will be tolerated between a particular antisense oligonucleotide and a particular CIF130 coding sequence.

CIF130 antisense oligonucleotides can be modified without affecting their ability to hybridize to a CIF130 coding sequence. These modifications can be internal or at one or both ends of the antisense molecule. For example, internucleoside phosphate linkages can be modified by adding cholesteryl or diamine moieties with varying numbers of carbon residues between the amino groups and terminal ribose. Modified bases and/or sugars, such as arabinose instead of ribose, or a 3', 5'-substituted oligonucleotide in which the 3' hydroxyl group or the 5' phosphate group are substituted, can also be employed in a modified antisense oligonucleotide. These modified oligonucleotides can be prepared by methods well known in the art. See, e.g., Agrawal et al., 1992, *Trends Biotechiol.* 10: 152–158, Uhlmann et al., 1990, *Chem. Rev.* 90:543–584, Uhlmann et al., 1987, *Tetrahedron. Lett.* 215:3539–3542.

Antibodies of the invention which specifically bind to a CIF130 protein, particularly single-chain antibodies, can also be used to alter CIF130 gene expression. CIF130-specific antibodies bind to CIF130 protein and prevent the protein from functioning in the cell. Polynucleotides encoding single-chain antibodies of the invention can be introduced into cells as described above.

Preferably, the mechanism used to decrease expression of the CIF130 gene, whether ribozyme, antisense nucleotide sequence, or antibody, decreases expression of the CIF130 gene by 50%, 60%, 70%, or 80%. Most preferably, expression of the CIF130 gene is decreased by 90%, 95%, 99%, or 100%. The effectiveness of the mechanism chosen to alter expression of the CIF130 gene can be assessed using methods well known in the art, such as hybridization of nucleotide probes to CIF130 mRNA, quantitative RT-PCR, or detection of CIF130 protein using CIF130-specific antibodies of the invention.

Compositions comprising CIF130 antibodies, ribozymes, or antisense oligonucleotides can be used to increase the number of cells in a cell population iii vitro or for treating disorders characterized by lowered rates of mitosis, such as anemia. CIF130 compositions of the invention can optionally comprise a pharmaceutically acceptable carrier. Pharmaceutically acceptable carriers are well known to those in the art. Such carriers include, but are not limited to, large, slowly metabolized macromolecules, such as proteins, polysaccharides, polylactic acids, polyglycolic acids, polymeric amino acids, amino acid copolymers, and inactive virus particles. Pharmaceutically acceptable salts can also be used in CIF130 compositions, for example, mineral salts such as hydrochlorides, hydrobromides, phosphates, or sulfates, as well as salts of organic acids such as acetates, proprionates, malonates, or benzoates. CIF130 compositions can also contain liquids, such as water, saline, glycerol, and ethanol, as well as substances such as wetting agents, emulsifying agents, or pH buffering agents. Liposomes, such as those described in U.S. Pat. No. 5,422,120, WO 95/13796, WO 91/14445, or EP 524,968 B1, can also be used as a carrier for a CIF130 composition.

Typically, a CIF130 composition is prepared as an injectable, either as a liquid solution or suspension; however, solid forms suitable for solution or suspension in liquid vehicles prior to injection can also be prepared. A CIF130 composition can also be formulated into an enteric coated tablet or gel capsule according to known methods in the art, such as those described in U.S. Pat. No. 4,853,230, EP 225,189, AU 9,224,296, and AU 9,230,801.

Alternatively, a composition comprising all or a portion of a CIF130 gene or expression product can be introduced into a cell in order to suppress or decrease mitosis or cell cycle progression. Such compositions can also comprise a pharmaceutically acceptable carrier, as described above. Proliferative disorders, such as neoplasias, dysplasias, and hyperplasias, and their symptoms can be treated by administration of a CIF130 composition comprising coding sequences for CIF130 or comprising CIF130 proteins or protein fragments. Neoplasias which can be treated with such CIF130 compositions include, but are not limited to, melanomas, squamous cell carcinomas, adenocarcinomas, hepatocellular carcinomas, renal cell carcinomas, sarcomas, myosarcomas, non-small cell lung carcinomas, leukemias, lymphomas, osteosarcomas, central nervous system tumors such as gliomas, astrocytomas, oligodendrogliomas, and neuroblastomas, tumors of mixed origin, such as Wilms' tumor and teratocarcinomas, and metastatic tumors. Proliferative disorders which can be treated with a CIF130 composition comprising CIF130 coding sequences or CIF130 proteins or polypeptides include disorders such as anhydric hereditary ectoderrnal dysplasia, congenital alveolar dysplasia, epithelial dysplasia of the cervix, fibrous dysplasia of bone, and mammary dysplasia. Hyperplasias, for example, endometrial, adrenal, breast, prostate, or thyroid hyperplasias, or pseudoepitheliomatous hyperplasia of the skin can be treated with such CIF130 compositions.

An entire CIF130 coding sequence or protein can be introduced, as described above. Alternatively, a portion of a CIF130 protein which binds to CIF150/hTAF$_{II}$150 and inhibits mitosis or cell cycle progression can be identified and that portion or a nucleotide sequence encoding it can be introduced into the cell. Portions of a CIF130 protein which result in decreased mitosis or cell cycle progression can be identified by introducing expression constructs which express different portions of the protein into cells and measuring alterations in the rate of mitosis. Rates of mitosis can be measured, for example, by detecting incorporation of labeled nucleotides, as is known in the art.

Even in disorders in which CIF130 mutations are not implicated, increasing CIF130 function can have therapeutic application. In these disorders, increasing CIF130 expression or function can help to suppress tumors. Similarly, in tumors in which CIF130 expression is not aberrant, CIF130 upregulation or increase of CIF130 activity can help to suppress metastases.

CIF130 compositions which contain CIF130 subgenomic polynucleotides preferably contain an expression construct comprising a promoter and a polynucleotide segment encoding at least 17 contiguous amino acids of a CIF130 protein or protein variant. Within the expression construct, the polynucleotide segment is located downstream from the promoter, and transcription of the polynucleotide segment initiates at the promoter. A more complete description of gene transfer vectors, especially retroviral vectors, is contained in U.S. Ser. No. 08/869,309.

Administration of CIF130 compositions of the invention can include local or systemic administration, including injection, oral administration, particle gun, or catheterized administration, and topical administration. Various methods can be used to administer a CIF130 composition directly to a specific site in the body. For example, a small metastatic lesion can be located and an appropriate CIF130 composition injected several times in several different locations within the body of the lesion. Alternatively, arteries which serve a tumor can be identified, and a CIF130 composition can be injected into such an artery in order to deliver the composition to the tumor.

A tumor which has a necrotic center can be aspirated, and a CIF130 composition can be injected directly into the now empty center of the tumor. A CIF130 composition can also be administered directly to the surface of a tumor, for example, by topical application of the composition. X-ray imaging can be used to assist in certain of these delivery methods. Combination therapeutic agents, including a CIF130 protein, polypeptide, or subgenomic CIF130 polynucleotide together with other therapeutic agents, can be administered simultaneously or sequentially.

CIF130 compositions can be delivered to specific tissues using receptor-mediated targeted delivery. Receptor-mediated DNA delivery techniques are taught in, for example, Findeis et al. (1993), *Trends in Biotechnol.* 11, 202–05, Chiou et al. (1994), Gene Therapeutics: Methods and Applications of Direct Gene Transfer (J. A. Wolff, ed.); Wu & Wu (1988), *J. Biol. Chem.* 263, 621–24; Wu et al. (1994), *J. Biol. Chem.* 269, 542–46; Zenke et al. (1990), *Proc. Natl. Acad. Sci. U.S.A.* 87, 3655–59; Wu et al. (1991), *J. Biol. Chem.* 266, 338–42.

Alternatively, a CIF130 composition can be introduced into human cells ex vivo, and the cells then replaced into the human. Cells can be removed from a variety of locations including, for example, from a selected tumor or from an affected organ. A CIF130 composition can be inserted into non-tumorigenic cells, such as dermal fibroblasts or peripheral blood leukocytes. If desired, particular fractions of cells, such as T cell subsets or stem cells, can also be specifically removed from the blood (see, for example, PCT WO 91/16116). The removed cells can then be contacted with a CIF130 composition utilizing any of the above-described techniques, followed by the return of the cells to the human.

Both the dose of a particular CIF130 composition and the means of administering the composition can be determined based on specific qualities of the CIF130 composition, the condition, age, and weight of the patient, the progression of the particular disease being treated, and other relevant factors. If the composition contains CIF130 proteins, polypeptides, or antibodies, effective dosages of the composition are in the range of about 5 μg to about 50 μg/kg of patient body weight, about 50 μg to about 5 mg/kg, about 100 μg to about 500 μg/kg of patient body weight, and about 200 to about 250 μg/kg.

Compositions containing CIF130 subgenomic polynucleotides, including antisense oligonucleotides and ribozyme-or antibody-encoding sequences, can be administered in a range of about 100 ng to about 200 mg of DNA for local administration. Suitable concentrations range from about 500 ng to about 50 mg, about 1 μg to about 2 mg, about 5 μg to about 500 μg, and about 20 μg to about 100 μg of DNA. Factors such as method of action and efficacy of transformation and expression are considerations which will affect the dosage required for ultimate efficacy of the CIF130 composition. If greater expression is desired over a larger area of tissue, larger amounts of CIF130 compositions or the same amount administered successively, or several administrations to different adjacent or close tissue portions of, for example, a tumor site, may be required to effect a positive therapeutic outcome. In all cases, routine experimentation in clinical trials will determine specific ranges for optimal therapeutic effect.

Expression of an endogenous CIF130 gene in a cell can be altered by introducing in frame with the endogenous CIF130 gene a DNA construct comprising a CIF130 targeting sequence, a regulatory sequence, an exon, and an unpaired splice donor site by homologous recombination, such that a homologously recombinant cell comprising a new CIF130 transcription unit is formed. The new transcription unit can be used to turn the CIF130 gene on or off as desired. This method of affecting endogenous gene expression is taught in U.S. Pat. No. 5,641,670, which is incorporated herein by reference.

The targeting sequence is a segment of at least 10, 12, 15, 20, or 50 contiguous nucleotides selected from the nucleotide sequence shown in SEQ ID NO:1. The transcription unit is located upstream of a coding sequence of the endogenous CIF130 gene. The exogenous regulatory sequence directs transcription of the coding sequence of the CIF130 gene.

The present invention also provides a method of diagnosing or prognosing neoplasia or of identifying neoplastic tissue of a human. CIF130 mRNA is apparently overexpressed in tumors when total RNA is compared (see Example 2). Expression of a CIF130 gene can therefore be compared between a first tissue which is suspected of being neoplastic and a second tissue of the human which is normal. The first and second tissues can be obtained from the same human or from different humans. The normal tissue can be any tissue of the human, including, but not limited to, spleen, thymus, prostate, testis, ovary, small intestine, mucosal lining of the colon, peripheral blood leukocytes, heart, glial cells, placenta, lung, liver, skeletal muscle, kidney, pancreas, peripheral blood leukocytes, bone marrow, and appendix. The tissue suspected of being neoplastic can be derived from a different tissue type of the human, but preferably it is derived from the same tissue type, for example an intestinal polyp or other abnormal growth.

Overexpression of the CIF130 gene in the suspect tissue identifies the suspect tissue as neoplastic. Expression of CIF130 can be detected by measuring total CIF130 mRNA. Total RNA can be isolated from the two tissues, as is known in the art. One of skill in the art can readily determine differences in the size or amount of CIF130 mRNA transcripts between the two tissues that are compared, using Northern blots or in situ hybridization with nucleotide probes selected from the nucleotide sequence shown in SEQ ID NO:1. Overexpression of CIF130 mRNA in a tissue sample suspected of being neoplastic compared with the expression of CIF130 mRNA in a normal tissue is indicative of neoplasia.

Alternatively, CIF130 proteins can be compared between the two samples. Any method for analyzing proteins can be used to compare two CIF130 proteins from matched samples. The sizes of the CIF130 proteins in the two tissues can be compared, for example, using antibodies of the invention to detect CIF130 proteins in Western blots of protein extracts from the two tissues. Other changes, such as expression levels and subcellular localization, can also be detected immunologically. A higher CIF130 protein expression level in a tissue suspected of being neoplastic compared with the CIF130 protein expression level in a normal tissue is indicative of neoplasia.

Similarly, comparison of CIF130 gene sequences or of CIF130 gene expression products, e.g., mRNA and protein, between a tissue of a human which is suspected of being neoplastic and a normal tissue of a human can be used to diagnose or prognose neoplasia in the human. The CIF130 genes in the two tissues can be compared by any means known in the art. For example, the two genes can be sequenced, and the sequence of the CIF130 gene in the tissue suspected of being neoplastic can be compared with the wild-type CIF130 sequence in the normal tissue. The CIF130 genes or portions of the CIF130 genes in the two tissues can be amplified, for example, using nucleotide primers selected from the nucleotide sequence shown in SEQ ID NO:1 in the polymerase chain reaction (PCR) or other amplification technique. The amplified genes or portions of genes can be hybridized to nucleotide probes selected from the nucleotide sequence shown in SEQ ID NO:1. The nucleotide probes can be labeled by a variety of methods, such as radiolabeling, biotinylation, or coupling to fluorescent or chemiluminescent tags, and detected by standard methods known in the art. Comparisons of CIF130 mRNA or protein can be made as described above. A difference between the CIF130 gene (or a gene which regulates, for example, its expression, half-life, or degradation) in the two tissues which are compared indicates neoplasia in the tissue. The degree of overexpression of the CIF130 gene in the neoplastic tissue relative to wild-type expression of the gene in normal tissue, or differences in the amount of overexpression of the CIF130 gene in the neoplastic tissue over time, can be used to prognose the progression of the neoplasia in that tissue or to monitor the response of the neoplastic tissue to various therapeutic regimens.

A genetic predisposition to neoplasia in a human can be detected by comparing a wild-type CIF130 gene, mRNA, or protein with a CIF130 gene, mRNA, or protein in a fetal tissue. Fetal tissues which can be used for this purpose include, but are not limited to, amniotic fluid, chorionic villi, blood, and the blastomere of an in vitro-fereilized embryo. The wild-type CIF130 gene can be obtained from any tissue. The mRNA or protein can be obtained from a normal tissue of a human in which the CIF130 gene is expressed. Such tissues are disclosed above. Differences, such as alterations in the nucleotide sequence or size of the fetal CIF130 gene or mRNA, or alterations in the molecular weight, amino acid sequence, or relative abundance of fetal CIF130 protein, indicate a germline mutation in the CIF130 gene of the fetus which indicates a genetic predisposition to neoplasia.

Kits for use in the diagnostic methods described above are also provided. CIF130 diagnostic kits comprise reagents which specifically bind to a human CIF130 gene or expression product and which can be used in methods of the invention, such as CIF130 subgenomic polynucleotide probes or antibodies. Means for labeling the probes or antibodies, reagents for use in the methods, such as buffers, and instructions for using the kits can also be included.

The function of CIF130 as a negative regulator of the transcription factor CIF150/hTAF$_{11}$150 can be exploited to identify genes whose transcription is dependent on the presence of CIF130. Isolated RNA from the two populations can be compared to identify genes which are differentially transcribed in two cell populations. In one population of a cell type, such as HeLa or NIH 3T3 cells, expression of a CIF130 gene is unaltered; in the other population of the cell type, expression of a CIF130 gene is decreased. RNA can be isolated from the two populations by methods well known in the art.

Decreased CIF130 expression can be achieved, for example, using ribozymes, antisense oligonucleotide sequences, or antibodies, as described above. The effectiveness of the mechanism chosen to alter expression of the CIF130 gene can be assessed using methods well known in the art, such as hybridization of nucleotide probes to CIF130 mRNA or detection of CIF130 protein using specific antibodies.

Genes which are differentially transcribed in the two populations can be compared, for example, using differential display PCR. Differential display PCR can be carried out on the two populations of cells using methods well known in the art. See, e.g., Liang & Pardee, 1992, Science 257:967–71; Bauer et al., 1993, Nucl. Acids. Res. 21:4272–80; Bauer et al., 1994, PCR Methods Appl. 4:S97–108; and Liang et al., 1995, Meth. Enz. 254:304–21. Kits for performing differential display PCR are available, for example, from Display Systems Biotech.

Briefly, total RNA is isolated form the two populations of cells. The RNA is reverse transcribed to produce a cDNA population which represents an overlapping subset of the total expression profile of the cells in each population. Each subset cDNA population is amplified using PCR with an anchored primer and a group of arbitrary primers in the presence of radiolabeled dATP. Amplified products from the two populations of cells are separated by gel electrophoresis, and patterns of separated products are detected, as is known in the art.

Differences in the two patterns, such as the presence, absence, altered position within the gel, or amount of one or more cDNA species, indicates that the expression of one or more genes was altered in response to decreasing the expression of the CIF130 gene. Differentially displayed bands can be excised from the gel, reamplified, and identified by sequence analysis. Optionally, the sequences can be cloned before sequencing. Sequences of the differentially displayed bands can be compared with known sequences in databases to determine the identity of genes whose expression was altered in response to decreasing expression of CIF130.

The invention also provides means of identifying compounds which alter mitosis or cell cycle progression. A cell population is contacted with a test compound. A test compound can be a pharmacologic agent already known in the art or can be a compound previously unknown to have any pharmacological activity. A test compound can be naturally occurring or designed in the laboratory. It can be isolated from microorganisms, animals, or plants, and can be produced recombinantly, or synthesized by chemical methods known in the art.

The cell population can comprise any primary human cell or human cell line which expresses a CIF130 gene, as disclosed above. Methods of establishing cultures of primary human cells or of culturing cell lines are well known in the art.

Expression of the CIF130 gene in the cell population is detected. Means of detecting CIF130 gene expression, for example by measuring CIF130 mRNA or CIF130 protein, are disclosed above. Expression can be measured in a sample of the same cell population before and after contact with the test compound. Alternatively, control cell populations which have not been contacted with the test compound can be employed. A test compound which decreases expression of the CIF130 gene is identified as a potential compound for inducing mitosis or cell cycle progression. A test compound which increases expression of the CIF130 gene is identified as a potential compound for inhibiting mitosis or cell cycle progression.

The invention also provides methods for screening test compounds for the ability to interfere with the binding of CIF130 to CIF150/hTAF$_{II}$150. According to one method, a CIF130 and a CIF150/hTAF$_{II}$150 protein, or at least the domains of each protein necessary for the binding interaction, are incubated together in the presence of a test compound. In the absence of the test compound, the CIF150/hTAF$_{II}$150-binding domain of the CIF130 protein binds to the CIF130-binding domain of CIF150/hTAF$_{II}$150. The amount of bound and/or unbound proteins or binding domains is determined according to any technique known in the art, including any immunological technique. In order to facilitate the assay, one of the proteins or binding domains can be bound to a solid support, or can be labeled with a radiolabel, or other detectable label. A useful agent is identified which decreases the amount of CIF130 and/or CIF150/hTAF$_{II}$150 protein or binding domain which is bound or increases the amount of CIF130 and/or CIF150/hTAF$_{II}$150 protein or binding domain which is unbound. The CIF130 and CIF150/hTAF$_{II}$150 proteins or binding domains can be prebound prior to the introduction of the test compound, or the test compound can be contacted with one of the two proteins or binding domains prior to incubation.

In another embodiment, a two-hybrid assay is used to screen compounds which inhibit the interaction between the binding partners, CIF130 and CIF150/hTAF$_{II}$150. According to such an assay, a fusion protein of each of the binding partners is used. The fusion proteins can comprise full-length CIF130 or CIF150/hTAF$_{II}$150 proteins or at least the domains of each protein necessary for the binding interaction. One of the binding partners is fused to a DNA binding domain and the other is fused to a transcriptional activating domain. If the fusion protein comprising the CIF130 protein or CIF150/hTAF$_{II}$150-binding domain of the CIF130 protein comprises the transcriptional activating domain, then the fusion protein comprising the CIF150/hTAF$_{II}$150 protein or CIF130-binding domain of the CIF150/hTAF$_{II}$150 protein comprises the DNA binding domain. If the fusion protein comprising the CIF150/hTAF$_{II}$150 protein or CIF130-binding domain of the CIF150/hTAF$_{II}$150 protein comprises the transcriptional activating domain, then the fusion protein comprising the CIF130 protein or CIF150/hTAF$_{II}$150-binding domain of the CIF130 protein comprises the DNA binding domain. The two fusion proteins interact to reconstitute a sequence-specific transcriptional activating factor. Many DNA binding domains and transcriptional activating domains can be used in this system, including the DNA binding domains of GAL4, LexA, and the human estrogen receptor paired with the acidic transcriptional activating domains of GAL4 or the herpes virus simplex protein VP16.

The two fusion proteins are contained in a cell which also comprises a reporter gene. The reporter gene is sensitive to the activation of the reconstituted sequence-specific transcriptional activating factor. Suitable reporter genes whose expression can be conveniently detected include the E. coli lacZ gene, whose expression may be measured colorimetrically, and yeast selectable genes such as HIS3 or URA3:

In the absence of the test compound, the cell expresses the reporter gene. A test compound is added to the cell, and the effect on expression of the reporter gene is measured. A test compound which disrupts the binding of the respective binding domains of CIF130 and CIF150/hTAF$_{II}$150 will have a negative effect on the transcriptional activation ability of the reconstituted sequence-specific transcriptional activating factor. Thus, expression of the reporter gene will be decreased. Compounds which decrease expression of the reporter gene are potential inducers of mitosis or cell cycle progression. Compounds which increase expression of the reporter gene are potential inhibitors of mitosis or cell cycle progression.

The CIF150/hTAF$_{II}$150-binding domain of CIF130 and the CIF130-binding domain of CIF150/hTAF$_{II}$150 can be readily determined, for example, by testing various portions of each protein for the ability to bind to its partner. A variety of techniques can be used for this purpose, including but not limited to the yeast two-hybrid assay, affinity column chromatography, and polyacrylamide gel electrophoresis under non-reducing conditions.

CIF130 subgenomic polynucleotides can also be delivered to subjects for the purpose of screening for test compounds agents which are useful for enhancing transfer of CIF130 subgenomic polynucleotides to a cell, for example, by enhancing transfer of CIF130 subgenomic polynucleotides to the cell or for enhancing subsequent biological effects of the CIF130 subgenomic polynucleotides within the cell. Such biological effects include hybridization to complementary CIF130 mRNA and inhibition of its translation, expression of the CIF130 subgenomic polynucleotide to form CIF130 mRNA and/or CIF130 protein, and replication and integration of the CIF130 subgenomic polynucleotide. Test compounds which can be screened include any substances, whether natural products or synthetic, which can be administered to the subject. Libraries or mixtures of compounds can be tested. The compounds or substances can be those for which a pharmaceutical effect is previously known or unknown. The compounds or substances can be delivered before, after, or concomitantly with the CIF130 subgenomic polynucleotides. They can be administered separately or in admixture with the CIF130 subgenomic polynucleotides.

Integration of delivered CIF130 subgenomic polynucleotides can be monitored by any means known in the art. For example, Southern blotting of the delivered CIF130 subgenomic polynucleotides can be performed. A change in the size of the fragments of the delivered polynucleotides indicates integration. Replication of the delivered polynucleotides can be monitored inter alia by detecting incorporation of labeled nucleotides combined with hybridization to a CIF130 probe. Expression of a CIF130 subgenomic polynucleotide can be monitored by detecting production of CIF130 mRNA which hybridizes to the delivered polynucleotide or by detecting CIF130 protein. CIF130 protein can be detected immunologically or by activity, for example by detecting binding to CIF150/hTAF$_{II}$150. Thus, the delivery of CIF130 subgenomic polynucleotides according to the present invention provides an excellent system for screening test compounds for their ability to enhance transfer of CIF130 subgenomic polynucleotides to a cell, by enhancing delivery, integration, hybridization, expression, replication or integration in an animal, preferably a mammal, more preferably a human.

The complete contents of all references cited in this disclosure are incorporated herein by reference. The following is provided for exemplification purposes only and is not intended to limit the scope of the invention which has been described in broad terms above.

EXAMPLE 1

This example demonstrates purification of CIF130.

Extracts of HeLa cells were prepared as described in Dignam et al., 1983, *Nucl. Acids Res.* 11, 1495–89. The 0.1 M KCl flowthrough fraction of a DEAE-Sephacel column was then applied to a Mono Q column and eluted with a linear KCl gradient (40 ml; 0.1 to 1 M). The CIF150/hTAF$_{II}$150/CIF130-containing fractions were pooled and dialyzed against buffer A (20 mM HEPES, pH 7.9, 1 mM EDTA, 3 mM dithiothreitol, 1 mM phenylmethylsulfonyl fluoride, 20% glycerol) containing 0.1 M KCl. These fractions were supplemented with imidazole (final concentration, 20 mM in buffer A) and applied to a Ni-nitrilotriacetic acid (NTA)-agarose column (Qiagen). After being washed with 10 column volumes each of 20 mM imidazole and 35 mM imidazole, bound proteins were eluted with 100 mM imidazole.

CIF130 copurifies with CIF150/hTAF$_{II}$150. Purified CIF150/hTAF$_{II}$150 and CIF130 proteins were visualized by sodium dodecyl sulfate-6% polyacrylamide gel electrophoresis, followed by silver staining. CIF130 was separated from CIF150/hTAF$_{11}$150 by excising the CIF130-containing band from the SDS gel and eluting the CIF130 protein.

EXAMPLE 2

This example demonstrates upregulation of CIF130 mRNA in human brain tumors.

Total RNA was isolated from human tumor and normal tissues from four different donors. The tissues included normal and tumor samples of breast, uterus, fallopian tube, and ovary, in addition to brain. Twenty micrograms of total RNA was loaded per lane and run on a 1% denaturing formaldehyde gel. Visual inspection of the gel after ethidium bromide staining confirmed that there was less than 10% variation between the lanes. The gel was vacuum-blotted to a positively charged nylon membrane, and the blot was fixed by UV irradiation and baking.

The nylon membrane was incubated with a radiolabeled CIF130 probe. The results showed that CIF130 mRNA is upregulated in brain tumor tissue compared with normal tissues from four different patients.

Those skilled in the art will recognize, or be able to ascertain, using not more than routine experimentation, many equivalents to the specific embodiments of the invention described herein. Such specific embodiments and equivalents are intended to be encompassed by the following claims.

All patents, published patent applications and publications cited herein are incorporated by reference as if set forth fully herein.

What is claimed is:

1. A method to aid in the diagnosis or prognosis of neoplasia in a human, comprising the step of:
   comparing expression of a first CIF130 gene in a first tissue of a human suspected of being neoplastic with expression of a second CIF130 gene in a second tissue of a human which is normal, wherein increased expression of the first CIF130 gene relative to expression of the second CIF130 gene indicates neoplasia in the first tissue.

2. A method to aid in the diagnosis or prognosis of neoplasia in a human, comprising the step of:
   comparing a first human CIF130 gene, mRNA, or protein in a first tissue suspected of being neoplastic with a second human CIF130 gene, mRNA, or protein in a second tissue which is normal, wherein the second CIF130 gene has a coding sequence as shown in SEQ ID NO:1, wherein a difference between the first and second CIF130 genes, mRNAs, or proteins indicates neoplasia in the first tissue.

3. The method of claim 1 wherein said normal tissue is selected from the group consisting of spleen, thymus, prostate, testis, ovary, small intestine, mucosal lining of the colon, peripheral blood leukocytes, heart, glial cells, placenta, lung, liver, skeletal muscle, kidney, pancreas, bone marrow, and appendix.

4. The method of claim 1 wherein said tissue suspected of being neoplastic is derived from a different tissue type of the human than the normal tissue.

5. The method of claim 1 wherein the tissue suspected of being neoplastic is derived from the same tissue type as the normal tissue.

6. The method of claim 1 wherein said normal tissue is mucosal lining of the colon and said tissue suspected of being neoplastic is an intestinal polyp.

7. The method of claim 2 wherein the size of CIF130 mRNA transcripts is compared.

8. The method of claim 2 wherein the amount of CIF130 mRNA transcripts is compared.

9. The method of claim 2 wherein the size of CIF130 proteins is compared.

10. The method of claim 2 wherein the amount of CIF130 proteins is compared.

11. The method of claim 10 wherein the amount of CIF130 proteins is compared by detecting CIF130 proteins in protein extracts of the first and second tissues using antibodies capable of specifically binding to CIF130.

12. The method of claim 2, wherein the polynucleotide sequences of said first and second human CIF130 gene or mRNA are sequenced and the sequences are compared.

13. The method of claim 12 wherein said genes are amplified prior to sequencing.

14. The method of claim 12 wherein said genes are each hybridized to at least one polynucleotide probe comprising a polynucleotide sequence of SEQ ID NO:1.

15. The method of claim 12 wherein said genes are each hybridized to at least one polynucleotide probe comprising a polynucleotide sequence of SEQ ID NO:1, and said probe is detectably labeled.

16. The method of claim 15 wherein said label is selected from the group consisting of radiolabel, biotinylation, fluorescent tag, and chemiluminsecent tag.

* * * * *

SEQUENCE LISTING

<160> NUMBER OF SEQ ID NOS: 4

<210> SEQ ID NO 1
<211> LENGTH: 3825
<212> TYPE: DNA
<213> ORGANISM: Homo sapien

<400> SEQUENCE: 1

| | | | | | |
|---|---|---|---|---|---|
| gcttccccg | cctctccttc | ctcgcgccgc | cctggcccgg | ccctgtcgcg | catgaaaccc | 60 |
| gaggccctaa | gcgaggcgcg | ggcgccaaca | tcgtcgacgg | cgacgtcggt | atcgtcgtcc | 120 |
| agtcagtaac | cgtggtactt | gaccttattt | ccaccaggac | cgtgattcgc | tcctaaaccg | 180 |
| aaacctccaa | aacggtagtc | acgacccttt | ttcctccttg | ggtttgaggg | tgtcgtcagg | 240 |
| gtgtcacgga | aaccccgttg | gtcgagaaga | agacctaaac | ctttcagtcg | aggcggtgtc | 300 |
| gaaggaagaa | agatgtttta | acctagattc | gcccggttga | aactacttct | tttacggata | 360 |
| aaacttctac | tccttcttct | aagatcgttg | caactaaatg | gaatgtaagg | acgacttttg | 420 |
| agtggttgag | cggttgttaa | ggtaaggttc | ggtcatctaa | gactgtcgct | actactaggg | 480 |
| aacctccgta | agtaccgact | ccacctccta | gtccgccgat | ctctgtactt | ctccgaactt | 540 |
| ctttcctgt | tcctttcttt | tttgcatttc | ccataagctc | tactgtaact | tctccttcta | 600 |
| ctggttcttc | gaataaaagc | tatgtaccgt | cttttgggtt | gacgaccaca | ccaagtcctc | 660 |
| cttctccttc | tgttagatct | tatactatca | ctgcctttag | gttaacgtgg | atggtttttt | 720 |
| tagtaactag | gagaaggggg | gtaactagta | agtctctaac | tgataggtgg | taaacttttt | 780 |
| ttgaaaatgt | tactcgtact | tctctattgg | ttggagtgag | gtgtcgtcaa | ttatctagag | 840 |
| gccgtattcg | agttagaagc | ccagagacca | cgacgtggag | gatctggtcc | ttcatcgaaa | 900 |
| cgagtaaaac | ccaaactgct | tgttgaatac | gtggtctaag | cctttagact | tatgtgtgtc | 960 |
| gggtgaggtt | atgtcacggt | cccacacgga | caccgtaatt | caccatctct | gtactaacca | 1020 |
| taacggtttt | gtccatcacc | cttttgacgt | cggaagtaaa | ccgggtacaa | ctaagtatat | 1080 |
| tacctggtct | tcctcaacct | tggtccacta | cctggttaac | gtcactaaca | cacaggatgg | 1140 |
| tccctcgaaa | cggtcgtcta | ggtaggtctt | acattcgcca | aaccttttcg | tatattagaa | 1200 |
| gctagtcacc | ggcatatacc | tcctccctca | tacaccctcg | tccggttccg | ggaagtcctc | 1260 |
| ccccgtctct | aacaacacac | atggggtcca | gctgactatc | tagtacactt | tttctttcga | 1320 |
| tggttagaag | ttctcagag | aatggaacac | aaactacttc | gtctagctta | caaactgtac | 1380 |
| cctaaactca | tggttcaagc | taggtatcgt | tcagtacaag | caggactgtc | cgtctgagag | 1440 |
| aataaatcac | gttgaaaagc | cttcttctaa | cttttcaacc | ggtctctgta | ggactagctg | 1500 |
| ggataagctc | accacgtccc | tctataacct | tccgtttac | ttctacactg | tgtctaacac | 1560 |
| ctctaagagg | taagacctgg | atcatttacc | ttgaccgaat | gggccgcaga | ccatcttaaa | 1620 |
| tggagaagtc | cctcacagga | ggagaaacaa | tgatttttc | ggttacgact | tctcgatcgc | 1680 |
| ttattggaat | ttgtcctccc | agtattagaa | cccgacgagg | taccctata | cctagtctca | 1740 |
| ctctctttgt | tccagtaaag | tctgaaattc | ttttcctgt | agggtcagga | ccaccggtgt | 1800 |
| ctacaacgtc | gggcaccaga | cctgtaagga | agttaattct | gacagtaatt | gatactacac | 1860 |
| cgtgccctgt | aactatgcgt | gtgagtgtcc | taaccggcgt | gtccttctcg | cccactcttt | 1920 |
| ccacaccgga | tatgggatga | gtgagggttc | ctgtcgttaa | aacgaccact | ggaccaggcc | 1980 |
| ttgaaccttc | ctcggttagt | tgtgcaaaga | ttccttgagg | atctagaccg | ttacgtctta | 2040 |

```
cggaccaaag cctttagagc taagtttcct ccctttcctt ttttcgactt gtaaccacct   2100
cctccggatc cgatgtccct cgccggaccg gacccgagac tcttgtacct agctccttta   2160
ttgttacatt actcgttaat actccggatg ttcggaaggt gtcctcgata ccctctagct   2220
gattgccgtt actttcgtcg aaaggtcagt gtcatgttct cagtgaaaca acgtcggtca   2280
aattcattag tcttccgacc ttcaagacga cggcccgtt cacccacctg atcacgtccc   2340
tcgaacttaa gacaaggttg attgagtcgt gttgtcccgg tattgtcagg actgtcgggg   2400
cagtggtcac ggcggttccc gtagggtccg aaaccgttat gaccgttgta gtcaccacgg   2460
ggacactgga tgggcagacg gcctcgggtt cctcagttgt tgtgtcgaag tcccttattg   2520
tcggctcttc cctgaccccc gtcgttgccc ttttccctct ctatatgact cttggccccg   2580
tcgtcggcag tgtcagtgcc tctctgaccg ttagccgtat cgctatcagg tgcagtgcct   2640
ctaccaccag cggtacctct acctatggcg gtaggtcttt cgtcgtcggc agtatgacta   2700
ccggtagccg tgcccctctt gtctgtacct ccttcgcgtc cggccgtacc cctcttggcc   2760
ccacgtttac taccagcctt accccttcg tcctttcttc gaaaattagc actcccgttc   2820
tacctcgggt tctaccttgg gtttcgcctg tcgtcgttct acctgttcca cctgtcgttc   2880
tgtctattct gtcgactgcc aaaacgacag ggtctcggcg gatttgcgtt ctttccagct   2940
accctgtcaa tctcccctac acgatttcgc actttagtca acaggaatta aaaatctttc   3000
taaaaccatt gatccacaga gtcccgaccc aaccccaggt ttcacattcc tgggggacgg   3060
gaatcacctc tcgacctcga acctctgtaa tggggaagta gtcttcctta aaagcctaca   3120
aaagaaccct tcgacaaaac caggaacctt cgtcactctc gaccctttcga agaaaaccga   3180
gatccactca acagtacgcc cattcaactc caatagaacc ctatttccca gaagatcccg   3240
tgttttgagt gagatccaaa tataatatac atcgaatata aaaatgatt ccacagtgga   3300
atattcgtag atatttaact caagaaaaag aatcaacata ccggtccgtc aggggtaaaa   3360
tcctcaaccg aagacgttta agttaggtaa ctcgattgac aaccctcgt taaccatca    3420
acatctgtaa acgtcccttc cctctacaga ctaagattta ccctcaacta cgagtccagg   3480
ggtcggtcca aacgtaggtc gggactctgt acatcctttg tggaaagtct gggtccgaga   3540
cttctaaggg tcttcggtgt tcctaacttc ccttttccac taggaccatt gacaaggtcc   3600
taacgaggtc caaactctac cataacgatt taaattttaa tttgttctct gggttgttgt   3660
cgaaatttc acagaagata aagtaacata aaaaaaattg aacggggtta ctatctttc    3720
agaaaacgac tttactaaaa ctactaaaaa caaatagcaa atattttttcc ttttctttat   3780
atttttttt tttttttttt tttttttttt cgccggcgac ttaag                     3825
```

<210> SEQ ID NO 2
<211> LENGTH: 1261
<212> TYPE: PRT
<213> ORGANISM: Homo sapien

<400> SEQUENCE: 2

Arg Arg Gly Arg Arg Gly Arg Ser Ala Ala Gly Pro Gly Arg Asp Ser
 1               5                  10                  15

Ala Tyr Phe Gly Leu Arg Asp Ser Leu Arg Ala Arg Gly Cys Ser Ser
             20                  25                  30

Cys Arg Cys Ser His Ser Ser Arg Ser Val Ile Gly Thr Met Asn Trp
         35                  40                  45

-continued

```
Asn Lys Gly Gly Pro Gly Thr Lys Arg Gly Phe Gly Phe Gly Gly Phe
 50                  55                  60
Ala Ile Ser Ala Gly Lys Lys Glu Pro Lys Leu Pro Gln Gln Ser
 65                  70                  75                  80
His Ser Ala Phe Gly Ala Thr Ser Ser Ser Gly Phe Gly Lys Ser
                 85                  90                  95
Ala Pro Pro Gln Leu Pro Ser Phe Tyr Lys Ile Gly Ser Lys Arg Ala
                100                 105                 110
Asn Phe Asp Glu Glu Asn Ala Tyr Phe Glu Asp Glu Glu Asp Ser
        115                 120                 125
Ser Asn Val Asp Leu Pro Tyr Ile Pro Ala Glu Asn Ser Pro Thr Arg
    130                 135                 140
Gln Gln Phe His Ser Lys Pro Val Asp Ser Asp Ser Asp Asp Asp Pro
145                 150                 155                 160
Leu Glu Ala Phe Met Ala Glu Val Glu Asp Gln Ala Ala Arg Asp Met
                165                 170                 175
Lys Arg Leu Glu Glu Lys Asp Lys Glu Arg Lys Asn Val Lys Gly Ile
                180                 185                 190
Arg Asp Asp Ile Glu Glu Glu Asp Gln Glu Ala Tyr Phe Arg Tyr
        195                 200                 205
Met Ala Glu Asn Pro Thr Ala Gly Val Val Gln Glu Glu Glu Asp
    210                 215                 220
Asn Leu Glu Tyr Asp Ser Asp Gly Asn Pro Ile Ala Pro Thr Lys Lys
225                 230                 235                 240
Ile Ile Asp Pro Leu Pro Pro Ile Asp His Ser Glu Ile Asp Tyr Pro
                245                 250                 255
Pro Phe Glu Lys Asn Phe Tyr Asn Glu His Glu Glu Ile Thr Asn Leu
                260                 265                 270
Thr Pro Gln Gln Leu Ile Asp Leu Arg His Lys Leu Asn Leu Arg Val
            275                 280                 285
Ser Gly Ala Ala Pro Pro Arg Pro Gly Ser Ser Phe Ala His Phe Gly
        290                 295                 300
Phe Asp Glu Gln Leu Met His Gln Ile Arg Lys Ser Glu Tyr Thr Gln
305                 310                 315                 320
Pro Thr Pro Ile Gln Cys Gln Gly Val Pro Val Ala Leu Ser Gly Arg
                325                 330                 335
Asp Met Ile Gly Ile Ala Lys Thr Gly Ser Gly Lys Thr Ala Ala Phe
                340                 345                 350
Ile Trp Pro Met Leu Ile His Ile Met Asp Gln Lys Glu Leu Glu Pro
            355                 360                 365
Gly Asp Gly Pro Ile Ala Val Ile Val Cys Pro Thr Arg Glu Leu Cys
    370                 375                 380
Gln Gln Ile His Pro Glu Cys Lys Arg Phe Gly Lys Ala Tyr Asn Leu
385                 390                 395                 400
Arg Ser Val Ala Val Tyr Gly Gly Gly Ser Met Trp Glu Gln Ala Lys
                405                 410                 415
Ala Leu Gln Glu Gly Ala Glu Ile Val Val Cys Thr Pro Gly Arg Leu
                420                 425                 430
Ile Asp His Val Lys Lys Lys Ala Thr Asn Leu Gln Arg Val Ser Tyr
        435                 440                 445
Leu Val Phe Asp Glu Ala Asp Arg Met Phe Asp Met Gly Phe Glu Tyr
    450                 455                 460
```

-continued

```
Gln Val Arg Ser Ile Ala Ser His Val Arg Pro Asp Arg Gln Thr Leu
465                 470                 475                 480

Leu Phe Ser Ala Thr Phe Arg Lys Lys Ile Glu Lys Leu Ala Arg Asp
            485                 490                 495

Ile Leu Ile Asp Pro Ile Arg Val Val Gln Gly Asp Ile Gly Glu Ala
            500                 505                 510

Asn Glu Asp Val Thr Gln Ile Val Glu Ile Leu His Ser Gly Pro Ser
        515                 520                 525

Lys Trp Asn Trp Leu Thr Arg Arg Leu Val Glu Phe Thr Ser Ser Gly
    530                 535                 540

Ser Val Leu Leu Phe Val Thr Lys Lys Ala Asn Ala Glu Glu Leu Ala
545                 550                 555                 560

Asn Asn Leu Lys Gln Glu Gly His Asn Leu Gly Leu Leu His Gly Asp
            565                 570                 575

Met Asp Gln Ser Glu Arg Asn Lys Val Ile Ser Asp Phe Lys Lys Lys
        580                 585                 590

Asp Ile Pro Val Leu Val Ala Thr Asp Val Ala Ala Arg Gly Leu Asp
    595                 600                 605

Ile Pro Ser Ile Lys Thr Val Ile Asn Tyr Asp Val Ala Arg Asp Ile
    610                 615                 620

Asp Thr His Thr His Arg Ile Gly Arg Thr Gly Arg Ala Gly Glu Lys
625                 630                 635                 640

Gly Val Ala Tyr Thr Leu Leu Thr Pro Lys Asp Ser Asn Phe Ala Gly
            645                 650                 655

Asp Leu Val Arg Asn Leu Glu Gly Ala Asn Gln His Val Ser Lys Glu
            660                 665                 670

Leu Leu Asp Leu Ala Met Gln Asn Ala Trp Phe Arg Lys Ser Arg Phe
        675                 680                 685

Lys Gly Gly Lys Gly Lys Lys Leu Asn Ile Gly Gly Gly Leu Gly
    690                 695                 700

Tyr Arg Glu Arg Pro Gly Leu Gly Ser Glu Asn Met Asp Arg Gly Asn
705                 710                 715                 720

Asn Asn Val Met Ser Asn Tyr Glu Ala Tyr Lys Pro Ser Thr Gly Ala
            725                 730                 735

Met Gly Asp Arg Leu Thr Ala Met Lys Ala Ala Phe Gln Ser Gln Tyr
        740                 745                 750

Lys Ser His Phe Val Ala Ala Ser Leu Ser Asn Gln Lys Ala Gly Ser
    755                 760                 765

Ser Ala Ala Gly Ala Ser Gly Trp Thr Ser Ala Gly Ser Leu Asn Ser
    770                 775                 780

Val Pro Thr Asn Ser Ala Gln Gln Gly His Asn Ser Pro Asp Ser Pro
785                 790                 795                 800

Val Thr Ser Ala Ala Lys Gly Ile Pro Gly Phe Gly Asn Thr Gly Asn
            805                 810                 815

Ile Ser Gly Ala Pro Val Thr Tyr Pro Ser Ala Gly Ala Gln Gly Val
        820                 825                 830

Asn Asn Thr Ala Ser Gly Asn Ser Arg Glu Gly Thr Gly Gly Ser
        835                 840                 845

Asn Gly Lys Arg Glu Arg Tyr Thr Glu Asn Arg Gly Ser Ser Arg His
    850                 855                 860

Ser His Gly Glu Thr Gly Asn Arg His Ser Asp Ser Pro Arg His Gly
865                 870                 875                 880
```

```
Asp Gly Gly Arg His Gly Asp Gly Tyr Arg His Pro Glu Ser Ser Ser
                885                 890                 895

Arg His Thr Asp Gly His Arg His Gly Glu Asn Arg His Gly Gly Ser
            900                 905                 910

Ala Gly Arg His Gly Glu Asn Arg Gly Ala Asn Asp Gly Arg Asn Gly
            915                 920                 925

Glu Ser Arg Lys Glu Ala Phe Asn Arg Glu Gly Lys Met Glu Pro Lys
            930                 935                 940

Met Glu Pro Lys Ala Asp Ser Ser Lys Met Asp Lys Val Asp Ser Lys
945                 950                 955                 960

Thr Asp Lys Thr Ala Asp Gly Phe Ala Val Pro Glu Pro Pro Lys Arg
            965                 970                 975

Lys Lys Gly Arg Trp Asp Ser Arg Gly Cys Ala Lys Ala Asn Gln Leu
            980                 985                 990

Ser Leu Ile Phe Arg Lys Ile Leu Val Thr Arg Cys Leu Arg Ala Gly
            995                 1000                1005

Leu Gly Ser Lys Val Gly Pro Pro Ala Leu Ser Gly Glu Leu Glu Leu
            1010                1015                1020

Gly Asp Ile Thr Pro Ser Ser Glu Gly Ile Phe Gly Cys Phe Leu Gly
1025                1030                1035                1040

Lys Leu Phe Trp Ser Leu Glu Ala Val Arg Ala Gly Lys Leu Leu Leu
            1045                1050                1055

Ala Leu Gly Glu Leu Ser Cys Gly Val Glu Val Ile Leu Gly Arg Val
            1060                1065                1070

Phe Gly Thr Lys Leu Thr Leu Gly Leu Tyr Tyr Met Leu Ile Phe Phe
            1075                1080                1085

Thr Lys Val Ser Pro Tyr Lys His Leu Ile Glu Phe Phe Phe Leu Val
            1090                1095                1100

Val Trp Pro Gly Ser Pro His Phe Arg Ser Trp Leu Leu Gln Ile Gln
1105                1110                1115                1120

Ser Ile Glu Leu Thr Val Gly Glu Gln Phe Gly Ser Cys Arg His Leu
            1125                1130                1135

Gln Gly Arg Glu Met Ser Asp Ser Lys Trp Glu Leu Met Leu Arg Ser
            1140                1145                1150

Pro Ala Arg Phe Ala Ser Ser Pro Glu Thr Cys Arg Lys His Leu Ser
            1155                1160                1165

Asp Pro Gly Ser Glu Asp Ser Gln Lys Pro Gln Gly Leu Lys Gly Lys
            1170                1175                1180

Gly Asp Pro Gly Asn Cys Ser Arg Ile Ala Pro Gly Leu Arg Trp Tyr
1185                1190                1195                1200

Cys Ile Asn Thr Arg Asp Pro Thr Thr Ala Phe Lys Val Ser Ser Ile
            1205                1210                1215

Ser Leu Tyr Phe Phe Leu Ala Pro Met Ile Glu Lys Ser Phe Ala Glu
            1220                1225                1230

Met Ile Leu Met Ile Phe Val Tyr Arg Leu Lys Gly Lys Glu Ile Lys
            1235                1240                1245

Lys Lys Lys Lys Lys Lys Lys Ala Ala Ala Glu Phe
            1250                1255                1260

<210> SEQ ID NO 3
<211> LENGTH: 3996
<212> TYPE: DNA
<213> ORGANISM: Homo sapien
```

-continued

```
<400> SEQUENCE: 3
caagatgtcg gcggatggta gcttcgagcc cttgcggaga ggagcatctc tgtgacagaa     60
gcttgtcgac ggcggcttct aggagctagt cgaaggagcg aggttgaggc gggcagcgac    120
ccgtcaggtc gctcacctgg gcaccggcca gctgcgagac gtgacttggg gaccgcaggg    180
gagtggagag tgtgaggtgc caaagactag taatgcccg tatcccccta ggaagccggg     240
aagccaagct ccgcgggacc gcttcatgcc gctgactggt gtagagcccg ccagaatgaa    300
caggaagaaa ggagacaagg gctttgaaag cccaaggcca tataaattaa cccatcaggt    360
cgtctgcatc aacaacataa atttccacag aaaatctgtt gtgggatttg tggaactgac    420
tatattcccc acagttgcaa acttgaatag aatcaagttg aacagcaaac agtgtagaat    480
ataccgagta aggatcaatg atttagaggc tgcttttatt tataatgacc caaccttgga    540
agtttgtcac agtgaatcaa aacagagaaa cctcaattat ttttccaatg cttatgcagc    600
tgcagttagt gctgtggacc ctgatgcagg aaatggagaa ctttgcatta aggttccatc    660
agagctatgg aaaacacgttg atgagttaaa ggtcctgaag atacacatca atttttcttt    720
ggatcagccc aaaggaggtc ttcattttgt ggtacccagt gtagagggaa gtatggcaga    780
gagaggtgct catgttttct cttgtgggta tcaaaattct acaagatttt ggttcccttg    840
tgttgattca tactctgaat tgtgtacatg gaaattagaa tttacagtag atgctgcaat    900
ggttgctgtt tctaatggcg atttggtgga gacagtgtat actctgata tgaggaagaa     960
aactttccat tatatgctta ccattcctac agcagcgtca aatatctcct tggccattgg   1020
accatttgaa atactggtag atccatacat gcatgaggtt actcattttt gtttgcccca   1080
acttcttcca ttgctgaaac ataccacatc ataccttcat gaagtctttg aattttatga   1140
agaaattctt acatgtcgtt acccatactc ctgttttaag actgtcttca ttgatgaggc   1200
ttatgttgaa gtggctgctt atgcttccat gagcattttt agcacaaatc ttttacacag   1260
tgccatgatt atagatgaga cacctttgac tagaaggtgt ttagcccaat ccttggccca   1320
gcagttttttt ggttgtttca tatctagaat gtcttggtct gatgaatggg tgctgaaggg   1380
aatttcaggc tatatctatg actttggat gaaaaaaact tttggtgtta atgagtaccg    1440
ccattggatt aaagaggagc tagacaaaat agtggcatat gaactaaaaa ctggtggggt   1500
tttactacat cccatatttg gtggaggaaa agagaaggat aatccggctt cccatctaca   1560
cttttcaata aagcatccac atacactgtc ctgggaatac tacactatgt ttcagtgtaa   1620
agcccaccct gtgatgagat tgattgaaaa taggatcagt atggaattta tgctacaagt   1680
tttcaataaa ctgctaagtc tggctagtac tgcttcatct cagaagttcc agtcacatat   1740
gtggagtcag atgttggttt ccacatctgg gttttttgaaa tccatttcaa atgtctctgg   1800
caaagatatt cagccgttaa taaagcagtg ggtagatcag agtggagtgg taaaattta    1860
tggaagtttt gcatttaata gaaaacgaaa tgtcttggaa ctggaaataa aacaggacta   1920
tacatctcct ggaactcaga aatacgtggg accacttaaa gtgacagtgc aggagttaga   1980
tggatccttc aatcatacac tgcaaattga agaaacagc cttaaacatg atatacccctg   2040
ccattccaaa agtagaagga ataaaaagaa aaaatccca ctgatgaatg gagaagaagt    2100
tgatatggat ctttctgcaa tggatgctga ttccccttg ctgtggataa ggatagaccc    2160
agatatgtca gtattgagga aggtagaatt tgagcaagct gatttttatgt ggcagtatca    2220
gctccgctat gagagagatg ttgttgcaca gcaggaatcc attttggctt tggaaaaatt    2280
ccctactcca gcatctcggc ttgcactcac tgatatatta gaacaagagc agtgtttcta   2340
```

-continued

```
cagagtaaga atgtcagctt gtttctgtct tgcaaagatt gcaaattcaa tggtgagcac      2400
atggacagga ccaccagcca tgaagtcact cttcactagg atgttttgtt gtaaaagttg      2460
tccaaacatt gtgaaaacaa acaactttat gagctttcaa agctattttc tacagaagac      2520
tatgccagtt gcaatggctt tattaagaga tgttcataat ctttgtccta agaagtctt       2580 aacatttatt ttagacttaa tcaagtacaa tgacaacagg aaaaataagt tttcagataa      2640
ctattatcgt gcagaaatga ttgatgccct ggccaactct gttacacctg cagtcagtgt      2700
gaataatgaa gttagaactt tggataactt aaatcctgat gtgcgactca ttcttgaaga      2760
aatcaccaga tttttgaata tggaaaaact tcttccgagt tacaggcata ccatcactgt      2820
cagttgtttg agagccatac gggtacttca gaagaacgga catgtgccaa gtgatccagc      2880 tcttttttaaa tcttatgctg aatatggcca ctttgtggac attaggatag cagctttgga    2940
agcagttgtt gattatacta aagtggacag aagttatgaa gaactgcaat ggctacttaa     3000
tatgattcag aatgaccctg taccctatgt aaggcataag attctcaaca tgttgactaa     3060 gaaccccca tttactaaga acatggagtc tcccttatgc aatgaagccc tggtagatca      3120
actttggaaa cttatgaatt ctggtacttc acatgactgg aggttacggt gtggtgctgt     3180
ggacttgtac ttcacacttt ttggcctcag tagaccttcc tgtttaccct tgccagagct    3240
tgggttggtt cttaatctaa aggagaaaaa agctgtcttg aatcctacca taattccaga    3300
gtcagtagca ggcaaccaag aagctgcaaa taatccaagc agtcacccac agctagttgg   3360
atttcagaac ccttttttcca gttctcaaga tgaggaggag attgatatgg atactgttca  3420
tgatagccag gccttcatttt cccatcattt aaacatgctt gaaaggccgt caactccagg  3480
gctctcgaaa tatcggccag ctagctcccg atctgcttta taccccagc actcagcagg    3540 ctgtgacagc acaccacca caaaacccca gtggagtttg aacttgcac ggaagggaac      3600 aggtaaagaa caagcaccct tggagatgag tatgcatcca gcggcaagcg ctccactctc    3660
agtctttact aaggaatcta cagcctccaa acacagtgac caccatcacc accatcacca    3720
tgagcacaag aaaaagaaga agaagcataa acataagcac aaacacaagc ataagcatga    3780
cagtaaagaa aaggacaagg agcctttcac tttctccagc cctgccagtg gcaggtctat    3840
tcgttctcct tcccttttcag actgagaagg ggacaaaaag acctttcctt tcatgtccag   3900
aagaatgtat gtaactaaag ctttgtcctc tgtgaagaat tataaatgga gggggaaag     3960 gattcgcctc tcctacagaa attctgaatt cattta                              3996
```

<210> SEQ ID NO 4
<211> LENGTH: 1199
<212> TYPE: PRT
<213> ORGANISM: Homo sapien

<400> SEQUENCE: 4

```
Met Pro Leu Thr Gly Val Glu Pro Ala Arg Met Asn Arg Lys Lys Gly
1               5                   10                  15

Asp Lys Gly Phe Glu Ser Pro Arg Pro Tyr Lys Leu Thr His Gln Val
            20                  25                  30

Val Cys Ile Asn Asn Ile Asn Phe His Arg Lys Ser Val Val Gly Phe
        35                  40                  45

Val Glu Leu Thr Ile Phe Pro Thr Val Ala Asn Leu Asn Arg Ile Lys
    50                  55                  60

Leu Asn Ser Lys Gln Cys Arg Ile Tyr Arg Val Arg Ile Asn Asp Leu
65                  70                  75                  80
```

```
Glu Ala Ala Phe Ile Tyr Asn Asp Pro Thr Leu Glu Val Cys His Ser
                85                  90                  95
Glu Ser Lys Gln Arg Asn Leu Asn Tyr Phe Ser Asn Ala Tyr Ala Ala
            100                 105                 110
Ala Val Ser Ala Val Asp Pro Asp Ala Gly Asn Gly Glu Leu Cys Ile
        115                 120                 125
Lys Val Pro Ser Glu Leu Trp Lys His Val Asp Glu Leu Lys Val Leu
    130                 135                 140
Lys Ile His Ile Asn Phe Ser Leu Asp Gln Pro Lys Gly Gly Leu His
145                 150                 155                 160
Phe Val Val Pro Ser Val Glu Gly Ser Met Ala Glu Arg Gly Ala His
                165                 170                 175
Val Phe Ser Cys Gly Tyr Gln Asn Ser Thr Arg Phe Trp Phe Pro Cys
                180                 185                 190
Val Asp Ser Tyr Ser Glu Leu Cys Thr Trp Lys Leu Glu Phe Thr Val
                195                 200                 205
Asp Ala Ala Met Val Ala Val Ser Asn Gly Asp Leu Val Glu Thr Val
            210                 215                 220
Tyr Thr His Asp Met Arg Lys Lys Thr Phe His Tyr Met Leu Thr Ile
225                 230                 235                 240
Pro Thr Ala Ala Ser Asn Ile Ser Leu Ala Ile Gly Pro Phe Glu Ile
                245                 250                 255
Leu Val Asp Pro Tyr Met His Glu Val Thr His Phe Cys Leu Pro Gln
                260                 265                 270
Leu Leu Pro Leu Leu Lys His Thr Thr Ser Tyr Leu His Glu Val Phe
            275                 280                 285
Glu Phe Tyr Glu Glu Ile Leu Thr Cys Arg Tyr Pro Tyr Ser Cys Phe
290                 295                 300
Lys Thr Val Phe Ile Asp Glu Ala Tyr Val Glu Val Ala Ala Tyr Ala
305                 310                 315                 320
Ser Met Ser Ile Phe Ser Thr Asn Leu Leu His Ser Ala Met Ile Ile
                325                 330                 335
Asp Glu Thr Pro Leu Thr Arg Arg Cys Leu Ala Gln Ser Leu Ala Gln
                340                 345                 350
Gln Phe Phe Gly Cys Phe Ile Ser Arg Met Ser Trp Ser Asp Glu Trp
            355                 360                 365
Val Leu Lys Gly Ile Ser Gly Tyr Ile Tyr Gly Leu Trp Met Lys Lys
        370                 375                 380
Thr Phe Gly Val Asn Glu Tyr Arg His Trp Ile Lys Glu Glu Leu Asp
385                 390                 395                 400
Lys Ile Val Ala Tyr Glu Leu Lys Thr Gly Gly Val Leu Leu His Pro
                405                 410                 415
Ile Phe Gly Gly Gly Lys Glu Lys Asp Asn Pro Ala Ser His Leu His
                420                 425                 430
Phe Ser Ile Lys His Pro His Thr Leu Ser Trp Glu Tyr Tyr Thr Met
            435                 440                 445
Phe Gln Cys Lys Ala His Leu Val Met Arg Leu Ile Glu Asn Arg Ile
    450                 455                 460
Ser Met Glu Phe Met Leu Gln Val Phe Asn Lys Leu Leu Ser Leu Ala
465                 470                 475                 480
Ser Thr Ala Ser Ser Gln Lys Phe Gln Ser His Met Trp Ser Gln Met
                485                 490                 495
```

-continued

```
Leu Val Ser Thr Ser Gly Phe Leu Lys Ser Ile Ser Asn Val Ser Gly
            500                 505                 510

Lys Asp Ile Gln Pro Leu Ile Lys Gln Trp Val Asp Gln Ser Gly Val
            515                 520                 525

Val Lys Phe Tyr Gly Ser Phe Ala Phe Asn Arg Lys Arg Asn Val Leu
            530                 535                 540

Glu Leu Glu Ile Lys Gln Asp Tyr Thr Ser Pro Gly Thr Gln Lys Tyr
545                 550                 555                 560

Val Gly Pro Leu Lys Val Thr Val Gln Glu Leu Asp Gly Ser Phe Asn
                565                 570                 575

His Thr Leu Gln Ile Glu Glu Asn Ser Leu Lys His Asp Ile Pro Cys
            580                 585                 590

His Ser Lys Ser Arg Arg Asn Lys Lys Lys Ile Pro Leu Met Asn
            595                 600                 605

Gly Glu Glu Val Asp Met Asp Leu Ser Ala Met Asp Ala Asp Ser Pro
            610                 615                 620

Leu Leu Trp Ile Arg Ile Asp Pro Asp Met Ser Val Leu Arg Lys Val
625                 630                 635                 640

Glu Phe Glu Gln Ala Asp Phe Met Trp Gln Tyr Gln Leu Arg Tyr Glu
                645                 650                 655

Arg Asp Val Val Ala Gln Gln Glu Ser Ile Leu Ala Leu Glu Lys Phe
            660                 665                 670

Pro Thr Pro Ala Ser Arg Leu Ala Leu Thr Asp Ile Leu Glu Gln Glu
            675                 680                 685

Gln Cys Phe Tyr Arg Val Arg Met Ser Ala Cys Phe Cys Leu Ala Lys
            690                 695                 700

Ile Ala Asn Ser Met Val Ser Thr Trp Thr Gly Pro Pro Ala Met Lys
705                 710                 715                 720

Ser Leu Phe Thr Arg Met Phe Cys Cys Lys Ser Cys Pro Asn Ile Val
                725                 730                 735

Lys Thr Asn Asn Phe Met Ser Phe Gln Ser Tyr Phe Leu Gln Lys Thr
            740                 745                 750

Met Pro Val Ala Met Ala Leu Leu Arg Asp Val His Asn Leu Cys Pro
            755                 760                 765

Lys Glu Val Leu Thr Phe Ile Leu Asp Leu Ile Lys Tyr Asn Asp Asn
            770                 775                 780

Arg Lys Asn Lys Phe Ser Asp Asn Tyr Tyr Arg Ala Glu Met Ile Asp
785                 790                 795                 800

Ala Leu Ala Asn Ser Val Thr Pro Ala Val Ser Val Asn Asn Glu Val
                805                 810                 815

Arg Thr Leu Asp Asn Leu Asn Pro Asp Val Arg Leu Ile Leu Glu Glu
            820                 825                 830

Ile Thr Arg Phe Leu Asn Met Glu Lys Leu Leu Pro Ser Tyr Arg His
            835                 840                 845

Thr Ile Thr Val Ser Cys Leu Arg Ala Ile Arg Val Leu Gln Lys Asn
            850                 855                 860

Gly His Val Pro Ser Asp Pro Ala Leu Phe Lys Ser Tyr Ala Glu Tyr
865                 870                 875                 880

Gly His Phe Val Asp Ile Arg Ile Ala Ala Leu Glu Ala Val Val Asp
                885                 890                 895

Tyr Thr Lys Val Asp Arg Ser Tyr Glu Glu Leu Gln Trp Leu Leu Asn
            900                 905                 910
```

```
Met Ile Gln Asn Asp Pro Val Pro Tyr Val Arg His Lys Ile Leu Asn
        915                 920                 925

Met Leu Thr Lys Asn Pro Pro Phe Thr Lys Asn Met Glu Ser Pro Leu
        930                 935                 940

Cys Asn Glu Ala Leu Val Asp Gln Leu Trp Lys Leu Met Asn Ser Gly
945                 950                 955                 960

Thr Ser His Asp Trp Arg Leu Arg Cys Gly Ala Val Asp Leu Tyr Phe
                965                 970                 975

Thr Leu Phe Gly Leu Ser Arg Pro Ser Cys Leu Pro Leu Pro Glu Leu
            980                 985                 990

Gly Leu Val Leu Asn Leu Lys Glu Lys Lys Ala Val Leu Asn Pro Thr
        995                 1000                1005

Ile Ile Pro Glu Ser Val Ala Gly Asn Gln Glu Ala Ala Asn Asn Pro
        1010                1015                1020

Ser Ser His Pro Gln Leu Val Gly Phe Gln Asn Pro Phe Ser Ser Ser
1025                1030                1035                1040

Gln Asp Glu Glu Glu Ile Asp Met Asp Thr Val His Asp Ser Gln Ala
                1045                1050                1055

Phe Ile Ser His His Leu Asn Met Leu Glu Arg Pro Ser Thr Pro Gly
            1060                1065                1070

Leu Ser Lys Tyr Arg Pro Ala Ser Ser Arg Ser Ala Leu Ile Pro Gln
        1075                1080                1085

His Ser Ala Gly Cys Asp Ser Thr Pro Thr Thr Lys Pro Gln Trp Ser
        1090                1095                1100

Leu Glu Leu Ala Arg Lys Gly Thr Gly Lys Glu Gln Ala Pro Leu Glu
1105                1110                1115                1120

Met Ser Met His Pro Ala Ala Ser Ala Pro Leu Ser Val Phe Thr Lys
                1125                1130                1135

Glu Ser Thr Ala Ser Lys His Ser Asp His His His His His His His
            1140                1145                1150

Glu His Lys Lys Lys Lys Lys His Lys His Lys His Lys His Lys Lys
        1155                1160                1165

His Lys His Asp Ser Lys Glu Lys Asp Lys Glu Pro Phe Thr Phe Ser
    1170                1175                1180

Ser Pro Ala Ser Gly Arg Ser Ile Arg Ser Pro Ser Leu Ser Asp
1185                1190                1195
```